(12) United States Patent
Wienhues-Thelen et al.

(10) Patent No.: US 10,488,422 B2
(45) Date of Patent: Nov. 26, 2019

(54) USE OF IGFBP-7 IN THE ASSESSMENT OF HEART FAILURE

(71) Applicants: Roche Diagnostics Operations, Inc., Indianapolis, IN (US); The Governing Council of the University of Toronto, Toronto (CA)

(72) Inventors: Ursula-Henrike Wienhues-Thelen, Krailling (DE); Georg Hess, Mainz (DE); Hendrik Huedig, Penzberg (DE); Herbert von der Eltz, Weilheim (DE); Andrew Emili, Toronto (CA); Anthony Gramolini, Toronto (CA); Peter Liu, Toronto (CA); David MacLennan, Toronto (CA); Vincent Fong, Auincourt (CA); Ruth Isserlin, Thornhill (CA); Thomas Kislinger, Toronto (CA); Dirk Block, Bichl (DE)

(73) Assignees: Roche Diagnostics Operations, Inc., Indianapolis, IN (US); The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 15/285,685

(22) Filed: Oct. 5, 2016

(65) Prior Publication Data
US 2017/0016918 A1    Jan. 19, 2017

Related U.S. Application Data

(63) Continuation of application No. 14/540,165, filed on Nov. 13, 2014, now abandoned, which is a continuation of application No. 12/504,208, filed on Jul. 16, 2009, now abandoned, which is a continuation of application No. PCT/EP2008/000576, filed on Jan. 25, 2008.

(30) Foreign Application Priority Data

Jan. 25, 2007 (EP) .................... 07001582

(51) Int. Cl.
G01N 33/53 (2006.01)
G01N 33/68 (2006.01)

(52) U.S. Cl.
CPC ..... *G01N 33/6893* (2013.01); *G01N 2333/47* (2013.01); *G01N 2333/4727* (2013.01); *G01N 2333/4737* (2013.01); *G01N 2333/4745* (2013.01); *G01N 2333/5412* (2013.01); *G01N 2333/58* (2013.01); *G01N 2800/325* (2013.01); *G01N 2800/56* (2013.01)

(58) Field of Classification Search
CPC .......... G01N 33/6893; G01N 2333/47; G01N 2333/4727; G01N 2333/4737; G01N 2333/4745; G01N 2333/5412; G01N 2333/58; G01N 2800/325; G01N 2800/56
See application file for complete search history.

(56) References Cited

U.S. PATENT DOCUMENTS

| | | | |
|---|---|---|---|
| 5,807,522 A | 9/1998 | Brown et al. | |
| 6,174,686 B1 | 1/2001 | Buechler et al. | |
| 6,333,397 B1 | 12/2001 | Katus et al. | |
| 6,376,206 B1 | 4/2002 | Katus et al. | |
| 6,403,764 B1 | 6/2002 | Dubaquie et al. | |
| 6,709,855 B1 | 3/2004 | Stanton et al. | |
| 7,632,647 B2 | 12/2009 | Dahlen et al. | |
| 2003/0119009 A1* | 6/2003 | Stuart ................ | C12N 15/1072 506/9 |
| 2003/0186308 A1 | 10/2003 | Young et al. | |
| 2004/0072238 A1 | 4/2004 | Yamano et al. | |
| 2005/0137481 A1 | 6/2005 | Sheard et al. | |
| 2006/0003338 A1 | 1/2006 | Deng et al. | |
| 2006/0063198 A1 | 3/2006 | Elgebaly | |
| 2007/0059767 A1 | 3/2007 | Karl et al. | |
| 2008/0254485 A1 | 10/2008 | Valkirs et al. | |
| 2009/0042228 A1 | 2/2009 | Hess et al. | |
| 2011/0104813 A1 | 5/2011 | Amann-Zalan et al. | |

FOREIGN PATENT DOCUMENTS

| | | |
|---|---|---|
| DE | 102005014752 A1 | 11/2006 |
| EP | 0394819 A3 | 4/1990 |
| WO | 1994/029448 A1 | 12/1994 |

(Continued)

OTHER PUBLICATIONS oiler, Alister, Diagnostic Horizons, Dynasciences Corportion, Published by Microbiological Associates, vol. 2, No. 1, Feb. 1978, pp. 1-7. V (Year: 1978) (Year: 1978).*

(Continued)

*Primary Examiner* — Gary Counts
(74) *Attorney, Agent, or Firm* — Dinsmore & Shohl LLP

(57) ABSTRACT

Disclosed is a method for assessing heart failure in vitro including the steps of measuring in a sample the concentration of the marker IGFBP-7, of optionally measuring in the sample the concentration of one or more other marker(s) of heart failure, and of assessing heart failure by comparing the concentration determined in for IGFBP-7 and the concentration(s) determined for the optionally one or more other marker to the concentration of this marker or these markers as established in a reference population. Also disclosed are the use of IGFBP-7 as a marker protein in the assessment of heart failure, a marker combination comprising IGFBP-7 and a kit for measuring IGFBP-7.

17 Claims, 6 Drawing Sheets

Specification includes a Sequence Listing.

(56) References Cited

FOREIGN PATENT DOCUMENTS

| WO | 2000/035473 A3 | 6/2000 |
| WO | 2000/045176 A3 | 8/2000 |
| WO | 2002/089657 A2 | 11/2002 |
| WO | 2003/054004 A3 | 7/2003 |
| WO | 2004/042000 A3 | 5/2004 |
| WO | 2004/099253 A1 | 11/2004 |
| WO | 2006/092729 A2 | 9/2006 |

OTHER PUBLICATIONS

Lopez-Bermejo et al., Characterization of Insulin-Like Growth Factor-Binding Proein-Related Proteins (IGFBP-rPs) 1, 2, 3 in Human Prostate Epithelia Cells: Potential Roles for IGFBP-rP1 and 2 in Senescence of the Prostatic Epithelium, Endocrinology, vol. 141, No. 11, 2000, pp. 4072-4080. (Year: 2000).*

Schmitt, Joachim P. et al., Dilated Cardiomyopathy and Heart Failure Caused by a Mutation in Phospholamban, Science, Feb. 28, 2003, pp. 1410-1413, vol. 299.

Smith, M. W. et al., Delayed metabolism of human brain natriuretic peptide reflects resistance to neutral endopeptidase, Journal of Endocrinology, 2000, pp. 239-246, vol. 167.

Sprenger, Cynthia C. et al., Insulin-like Growth Factor Binding Protein-related Protein 1 (IGFBP-rP1) Is a Potential Tumor Suppressor Protein for Prostate Cancer, Cancer Research, May 15, 1999, pp. 2370-2375, vol. 59.

St. Croix, Brad et al., Genes Expressed in Human Tumor Endothelium, Science, Aug. 18, 2000, pp. 1197-1202, vol. 289.

Tijssen, P., Practice and Theory of Enzyme Immunoassays, 1990, pp. 43-78 and pp. 108-115, Elsevier Science Publishers B.V., Amsterdam.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

Yamauchi, Teruaki et al., Purification and molecular cloning of prostacyclin-stimulating factor from serum-free conditioned medium of human diploid fibroblast cells, Biochemistry Journal, 1994, pp. 591-598, vol. 303.

Yuan, Guohui et al., "Proinflammatory cytokines in patents with congestive heart failure," Journal of Clinical Cardiology, 2004, pp. 263-265, vol. 20, No. 5, portions in English.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

Gerhardt et al., S-Tropinnin Tin suspected ischemic Myocardial Injury, Clinical Chemistry, 1991, pp. 1405-1411, vol. 37, No. 8.

International Search Report dated Mar. 27, 2008 in PCT Application No. PCT/EP2008/000576, 6 pages.

International Preliminary Report on Patentability dated Jul. 28, 2009 in PCT Application No. PCT/EP2008/000576, 10 pages.

Akaogi, Kotaro et al., Specific accumulation of tumor-derived adhesion factor in tumor blood vessels and in capillary tube-like structures of cultured vascular endothelial cells, Proceedings of the National Academy of Sciences, Aug. 1996, pp. 8384-8389, vol. 93.

Ashai, Michio et al., Cardiac-specific overexpression of sarcolipin inhibits sarco(endo)plasmic reticulum Ca2+ ATPase (SERCA2a) activity and impairs cardiac function in mice, Proceedings of the National Academy of Sciences, Jun. 22, 2004, pp. 9199-9204, vol. 101, No. 25.

Beck-Da-Silva, Luis et al., BNP-Guided Therapy Not Better Than Expert's Clinical Assessment for β-Blocker Titration in Patients With Heart Failure, Congestive Heart Failure, Sep.-Oct. 2005, pp. 248-253, vol. 11.

Benamer, Hakim et al., Comparison of the Prognostic Value of C-Reactive Protein and Troponin I in Patients With Unstable Angina Pectoris, American Journal of Cardiology, 1998, pp. 845-850, vol. 82.

Benjamin, Yoav and Hochberg, Yosef, Controlling the False Discovery Rate: a Practical and Powerful Approach to Multiple Testing, Journal of the Royal Statistical Society B, 1995, pp. 289-300, vol. 57, No. 1.

Breiman, Leo et al., Classification and Regression Trees, 1984, Wadsorth International Group, Belmont, California.

Breiman, Leo, Random Forests, Machine Learning, 2001, pp. 5-32, vol. 45.

Burger, Angelika M. et al., Down-regulation of T1A12/mac25, a novel insulin-like growth factor binding protein related to gene, is associated with disease progression in breast carcinomas, Oncogene, 1998, pp. 2459-2467, vol. 16.

Burmeister, G. et al., A Selective Method for Determining MRP8 and MRP14 Homocomplexes and Heterocomplexes by Sandwich ELISA for the Discrimination of Active and Non-Active Osteoarthritis from Rheumatoid Arthritis in SERA and Synovial Fluids, Inflammopharmacology, 1995, pp. 221-230, vol. 3.

Christenson, Robert H. et a., Cardiac troponin T and cardiac troponin I: relative values in short-term risk stratification of patients with acute coronary syndromes, Clinical Chemistry, 1998, pp. 494-501, vol. 44, No. 3.

Cleveland, William S. and Devlin, Susan J., Locally Weighted Regression: An Approach to Regression Analysis by Local Fitting, Journal of the American Statistical Association, Sep. 1988, pp. 596-610, vol. 83, No. 403.

De Tombe, Pieter P., Altered contractile function in heart failure, Cardiovascular Research, 1998, pp. 367-380, vol. 37.

Diamandis, Eleftherios P. and Christopoulos, Theodore K., Editors, Immunoassay, 1996, pp. 237-255, Chapter 11, Academic Press, London.

Duda, Richard O. et al., Pattern Classification, Second Edition, 2001, John Wiley & Sons, New York.

Etoh, Takashi et al., "Expression of prostacyclin-stimulating factor (PSF) in mononuclear cells of human peripheral blood and THP-1 derived macrophase-like cells, and effects of high glucose concentration," EXCLI Journal, 2005, pp. 141-151, vol. 4.

Foell, D. et al., Expression of the pro-inflammatory protein S100A12 (EN-RAGE) in rheumatoid and psoriatic arthritis, Rheumatology, 2003, pp. 1383-1389, vol. 42.

Friedman, Jerome H., Regularized Discriminant Analysis, Journal of the American Statistical Association, Mar. 1989, pp. 165-175, vol. 84, No. 405.

Gearing, Andrew J. H. et al., Soluble Forms of Vascular Adhesion Molecules, E-Selectin, ICAM-1, and VCAM-1: Pathological Significance, Annals New York Academy of Sciences, 1992, pp. 324-331, vol. 667.

Gremmler, Bernhard et al., Relation between N-terminal pro-brain natriuretic peptide values and invasively measured left ventricular hemodynamic indices, Experimental Clinical Cardiology, 2003, pp. 91-94, vol. 8, No. 2.

GroPep Bioreagents, IGFBP-rP1 antibody (Rabbit), 2013, pp. 1-2.

Gustafsson, Finn et al., Diagnostic and Prognostic Performance of N-Terminal ProBNP in Primary Care Patients With Suspected Heart Failure, Journal of Cardiac Failure, 2005 Supplement, pp. S15-S20, vol. 11, No. 5.

Hamm, Christian W. et al., The Prognostic Value of Serum Troponin T in Unstable Angina, The New England Journal of Medicine, Jul. 16, 1992, pp. 146-150, vol. 327.

Hastie, Trevor et al., The Elements of Statistical Learning Data Mining, Inference, and prediction, Springer Series in Statistics, 2001, Verlag, New York.

"Heart Disease and Stroke Statistics—2005 Update," American Heart Association, 2005, 63 pages, Dallas, Texas.

Hunt, P. J. et al., The Amino-Terminal Portion of Pro-Brain Natriuretic Peptide (Pro-BNP) Circulates in Human Plasma, Biochemical and Biophysical Research Communications, Sep. 25, 1995, pp. 1175-1183, vol. 214, No. 3.

Hunt, P. J. et al., The Role of the Circulation in Processing pro-Brain Natriuretic Peptide (proBNP) to Amino-Terminal BNP and BNP-32, Peptides, 1997, pp. 1475-1481, vol. 18, No. 10.

Hwa, Vivian et al., The Insulin-Like Growth Factor-Binding Protein (IGFBP) Superfamily, Endocrine Reviews, 1999, pp. 761-787, vol. 20, No. 6.

(56) References Cited

OTHER PUBLICATIONS

Jones, John I. and Clemmons, David R., Insulin-Like Growth Factors and Their Binding Proteins: Biological Actions, Endocrine Reviews, 1995, pp. 3-34, vol. 16, No. 1.

Katus, Hugo A. et al., Enzyme Linked Immuno Assay of Cardiac Troponin T for the Detection of Acute Myocardial Infarction in Patients, Journal of Molecular and Cellular Cardiology, 1989, pp. 1349-1353, vol. 21.

Kim, Ho-Seong et al., Identification of a family of low-affinity insulin-like growth factor binding proteins (IGFBPs): Characterization of connective tissue growth factor as a member of the IGFBP superfamily, Proceedings of the National Academy of Sciences, Nov. 1997, pp. 12981-12986, vol. 94.

Kislinger, Thomas, PRISM, a Generic Large Scale Proteomic Investigation Strategy for Mammals, Molecular & Cellular Proteomics, 2003, pp. 96-106, vol. 2, No. 2.

Lopez-Bermejo, Abel et al., Characterization of Insulin-Like Growth Factor-Binding Protein-Related Proteins (IGFBP-rPs) 1, 2, and 3 in Human Prostate Epithelial Cells: Potential Roles for IGFBP-rP1 and 2 in Senescence of the Prostatic Epithelium, Endocrinology, 2000, pp. 4072-4080, vol. 141.

Lopez-Bermejo, Abel et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues, The Journal of Clinical Endocrinology & Metabolism, 2003, pp. 3401-3408, vol. 88, No. 7.

Lopez-Bermejo, Abel et al., Insulin Resistance Is Associated With Increased Serum Concentration of IGF-Binding Protein-Related Protein 1 (IGFBP-rP1/MAC25), Diabetes, Aug. 2006, pp. 2333-2339, vol. 55.

McDonagh, T. A. et al., NT-proBNP and the diagnosis of heart failure: a pooled analysis of three European epidemiological studies, The European Journal of Heart Failure, 2004, pp. 269-273, vol. 6.

Missov, Emil and Mair, Johannes, "A novel biochemical approach to congestive heart failure: Cardiac troponin T," American Heart Journal, 1999, pp. 95-99, vol. 138.

Molkentin, Jeffery D. and Dorn, Gerald W. II, Cytoplasmic Signaling Pathways That Regulate Cardiac Hypertrophy, Annual Reviews in Physiology, 2001, pp. 391-426, vol. 63.

Mueller, Thomas et al., Long-term stability of endogenous B-type natriuretic peptide (BNP) and amino terminal proBNP (NT-proBNP) in frozen plasma samples, Clinical Chemistry Laboratory Medicine, 2004, pp. 942-944, vol. 42, No. 8.

Oh, Youngman et al., Synthesis and Characterization of Insulin-like Growth Factor-binding Protein (IGFBP)-7 Recombinant Human mac25 Protein Speficially Binds IGF-1 and -II, The Journal of Biological Chemistry, Nov. 29, 1996, pp. 30322-30325, vol. 271, No. 48.

Ohman, E. Magnus et al., Cardiac Troponin T Levels for Risk Stratification in Acute Myocardial Ischemia, The New England Journal of Medicine, Oct. 31, 1996, pp. 1333-1341, vol. 335, No. 18.

Ono, Yasuhiro et al., Expression of prostacyclin-stimulating factor, a novel protein, in tissues of Wistar rats and in cultured cells, Biochemical and Biophysical Research Communications, Aug. 15, 1994, pp. 1490-1496, vol. 22, No. 3.

Oudit, Gavin Y. et al., L-type Ca2+ channels provide a major pathway for iron entry into cardiomyocytes in iron-overload cardiomyopathy, Nature Medicine, Sep. 2003, pp. 1187-1194, vol. 9, No. 9.

Pepe, Margaret Sullivan, The Statistical Evaluation of Medical Tests for Classification and Prediction, 2003, Oxford University Press, New York.

Piano, Mariann R. et al., Cellular Events Linked to Cardiac Remodeling in Heart Failure: Targets for Pharmacologic Intervention, The Journal of Cardiovascular Nursing, Jul. 2000, pp. 1-23, vol. 14, No. 4.

Robinson, William H. et al., Autoantigen microarrays for multiplex characterization of autoantibody responses, Nature Medicine, Mar. 2002, pp. 295-301, vol. 8, No. 3.

Robinson, William H. et al., Proteomics Technologies for the Study of Autoimmune Disease, Arthritis & Rheumatism, Apr. 2002, pp. 885-893, vol. 46, No. 4.

Ruan, Wen-jing et al., "IGFBP7 plays a potential tumor suppressor role against colorectal carcinogenesis with its expression associated with DNA hypomethylation of exon 1," Journal of Zhejiang University Science B, 2006, pp. 929-932, No. 11.

Ruczinski, Ingo et al., Logic Regression, Journal of Computational and Graphical Statistics, 2003, pp. 475-511, vol. 12, No. 3.

Rosenfeld, Ron G., A Novel Member of the Insulin-like Growth Factor Binding Protein Superfamily in Prostate Cancer, Prepared for U. S. Army Medical Research and Material Command, 2004, 82 pps., http://oai.dtic.rnil/oai/oai?verb=getRecord&metadataPrefix=html&identifier=ADA438221, Contracting Organization Oregon Health Sciences University.

Wang Jiyao, People's Medical Publishing House, 3rd Printing of 1st Edition in Dec. 2006, pp. 187-188 and 190, English portions only.

\* cited by examiner

Cardiac function in AB mice and controls

USE OF IGFBP-7 IN THE ASSESSMENT OF HEART FAILURE

RELATED APPLICATIONS

This application is a continuation of U.S. application Ser. No. 14/540,165 filed Nov. 13, 2014, now abandoned, which is a continuation of U.S. application Ser. No. 12/504,208 filed Jul. 16, 2009, now abandoned, which is a continuation of PCT/EP2008/000576 filed Jan. 25, 2008, and claims priority to EP 07001582.1 filed Jan. 25, 2007, the disclosures of which are hereby incorporated by reference in their entirety.

FIELD OF THE INVENTION

The present invention relates to a method for assessing heart failure in an individual comprising the steps of a) measuring in a sample obtained from the individual the concentration of the marker insulin like growth factor binding protein 7 (IGFBP-7), of b) optionally measuring in the sample the concentration of one or more other marker(s) of heart failure, and of assessing heart failure by comparing the concentration determined in step (a) and optionally the concentration(s) determined in step (b) to the concentration of this marker or these markers as established in a control sample. Also disclosed are the use of IGFBP-7 as a marker protein in the assessment of heart failure, a marker combination comprising IGFBP-7 and a kit for measuring IGFBP-7.

BACKGROUND OF THE INVENTION

Heart failure (HF) is a major and growing public health problem. In the United States for example approximately 5 million patients have HF and over 550 000 patients are diagnosed with HF for the first time each year (In: American Heart Association, Heart Disease and Stroke Statistics: 2005 Update, Dallas, Tex., American Heart Association (2005)). Similarly US-statistics show that HF is the primary reason for 12 to 15 million office visits and 6.5 million hospital days each year. From 1990 to 1999, the annual number of hospitalizations has increased from approximately 810 000 to over 1 million for HF as a primary diagnosis and from 2.4 to 3.6 million for HF as a primary or secondary diagnosis. In 2001, nearly 53 000 patients died of HF as a primary cause. Heart failure is primarily a condition of the elderly, and thus the widely recognized "aging of the population" also contributes to the increasing incidence of HF. The incidence of HF approaches 10 per 1000 in the population after age 65. In the US alone, the total estimated direct and indirect costs for HF in 2005 were approximately $27.9 billion and approximately $2.9 billion annually is spent on drugs for the treatment of HF (cf. the above cited AHA-statistics).

Heart Failure

Heart failure is characterized by a loss in the heart's ability to pump as much blood as the body needs. Failure does not mean that the heart has stopped pumping but that it is failing to pump blood as effectively as it should.

The NYHA (New York Heart Association) and the ACC/AHA (American Association of Cardiology/American Heart Association) have both established functional classes of HF to gauge the progression of the disease. The NYHA classification scheme has four classes of disease state: Class 1 is asymptomatic at any level of exertion. Class 2 is symptomatic at heavy exertion and Classes III and IV are symptomatic at light and no exertion, respectively.

In the four stage ACC/AHA scheme, Stage A is asymptomatic but is at risk for developing HF. Stage B there is evidence of cardiac dysfunction without symptoms. In Stage C there is evidence of cardiac dysfunction with symptoms. In Stage D, the subject has symptoms of HF despite maximal therapy.

Etiology of Heart Failure

Medically, heart failure (HF) must be appreciated as being a complex disease. It may be caused by the occurrence of a triggering event such as a myocardial infarction (heart attack) or be secondary to other causes such as hypertension, diabetes or cardiac malformations such as valvular disease. Myocardial infarction or other causes of HF result in an initial decline in the pumping capacity of the heart, for example by damaging the heart muscle. This decline in pumping capacity may not be immediately noticeable, due to the activation of one or more compensatory mechanisms. However, the progression of HF has been found to be independent of the patient's hemodynamic status. Therefore, the damaging changes caused by the disease are present and ongoing even while the patient remains asymptomatic. In fact, the compensatory mechanisms which maintain normal cardiovascular function during the early phases of HF may actually contribute to progression of the disease in the long run, for example by exerting deleterious effects on the heart and its capacity to maintain a sufficient level of blood flow in the circulation.

Some of the more important pathophysiological changes which occur in HF are (i) activation of the hypothalamic-pituitary-adrenal axis, (ii) systemic endothelial dysfunction and (iii) myocardial remodeling.

(i) Therapies specifically directed at counteracting the activation of the hypothalamic-pituitary-adrenal axis include beta-adrenergic blocking agents (B-blockers), angiotensin converting enzyme (ACE) inhibitors, certain calcium channel blockers, nitrates and endothelin-1 blocking agents. Calcium channel blockers and nitrates, while producing clinical improvement have not been clearly shown to prolong survival, whereas B-blockers and ACE inhibitors have been shown to significantly prolong life, as have aldosterone antagonists. Experimental studies using endothelin-1 blocking agents have shown a beneficial effect.

(ii) Systemic endothelial dysfunction is a well-recognized feature of HF and is clearly present by the time signs of left ventricular dysfunction are present. Endothelial dysfunction is important with respect to the intimate relationship of the myocardial microcirculation with cardiac myocytes. The evidence suggests that microvascular dysfunction contributes significantly to myocyte dysfunction and the morphological changes which lead to progressive myocardial failure.

In terms of underlying pathophysiology, evidence suggests that endothelial dysfunction may be caused by a relative lack of NO which can be attributed to an increase in vascular $O_2$-formation by an NADH-dependent oxidase and subsequent excess scavenging of NO. Potential contributing factors to increased $O_2$-production include increased sympathetic tone, norepinephrine, angiotensin II, endothelin-1 and TNF-α. In addition, levels of IL-10, a key anti-inflammatory cytokine, are inappropriately low in relation to TNF-α levels. It is now believed that elevated levels of TNF-α, with associated proinflammatory cytokines including IL-6, and soluble TNF-α receptors, play a significant role in the evolution of HF by causing decreased myocardial contractility, biventricular dilatation, and hypotension and are probably involved in endothelial activation and dysfunction. It is also believed that TNF-α may play a role in the hitherto unexplained muscular wasting which occurs in severe HF patients. Preliminary studies in small numbers of patients with soluble TNF-receptor therapy have indicated improvements in NYHA functional classification and in patient well-being, as measured by quality of life indices.

(iii) Myocardial remodeling is a complex process which accompanies the transition from asymptomatic to symptomatic heart failure, and may be described as a series of adaptive changes within the myocardium, like alterations in ventricular shape, mass and volume (Piano, M. R., et al., J. Cardiovasc. Nurs. 14 (2000) 1-23; Molkentin, J. D., Ann. Rev. Physiol. 63 (2001) 391-426). The main components of myocardial remodeling are alterations in myocyte biology, like myocyte hypertrophy, loss of myocytes by necrosis or apoptosis, alterations in the extracellular matrix and alterations in left ventricular chamber geometry. It is unclear whether myocardial remodeling is simply the end-organ response that occurs following years of exposure to the toxic effects of long-term neurohormonal stimulation, or whether myocardial remodeling contributes independently to the progression of heart failure. Evidence to date suggests that appropriate therapy can slow or halt progression of myocardial remodeling.

Markers and Disease State

As indicated above, myocyte hypertrophy is likely to represent one of the first steps down the road to HF. Myocyte hypertrophy is characterized by an increased expression of some genes encoding contractile proteins, such as p-myosin heavy chain and troponin T (TnT), and of some non-contractile proteins, such as A-type and B-type natriuretic peptides, by an increased cell size and by cytoskeletal alteration (Piano, M. R., et al., J. Cardiovasc. Nurs. 14 (2000) 1-23; Molkentin, J. D., Ann. Rev. Physiol. 63 (2001) 391-426).

Studies of human and animal models of heart failure suggest depressed myocyte function in the later stages of cardiac failure. The mechanisms that underlie myocyte dysfunction have been suggested to involve alterations in the calcium-handling network, myofilament and cytoskeleton (de Tombe, P. P., Cardiovasc. Res. 37 (1998) 367-380). For example, in human and animal models of heart failure, sarcoplasmic reticulum calcium-ATPase enzyme activity is reduced, while both mRNA and protein levels of the sarcolemmal Na+/Ca2+ exchanger are increased. Moreover, there is isoform-switching of TnT, reduced phosphorylation of troponin I (TnI), decreased myofibrillar actomyosin ATPase activity and enhanced microtubule formation in both human and animal models of heart failure.

Initially the changes to the heart, leading to myocardial remodeling are meant to compensate for the diseased parts of the myocardium in order to sustain the body's demand for oxygen and nutrients. However, the compensatory phase of heart failure is limited, and, ultimately, the failing heart is unable to maintain cardiac output adequate to meet the body's needs. Thus, there is a transition from a compensatory phase to a decompensatory phase. In the decompensatory phase, the cascade of changes in the heart continues but is no longer beneficial, moving the patient down the progression of heart failure to a chronic state and eventual death.

According to the "ACC/AHA 2005 Guideline Update for the Diagnosis and Management of Chronic Heart Failure in the Adult", the disease continuum in the area of heart failure is nowadays grouped into four stages as noted above. In stages A and B the individuals at risk of developing heart failure are found, whereas stages C and D represent the groups of patients showing signs and symptoms of heart failure. Details for defining the different stages A through D as given in the above reference are hereby included by reference.

Diagnostic Methods in Heart Failure

The single most useful diagnostic test in the evaluation of patients with HF is the comprehensive 2-dimensional echocardiogram coupled with Doppler flow studies to determine whether abnormalities of myocardium, heart valves, or pericardium are present and which chambers are involved. Three fundamental questions must be addressed: 1) is the LVEF preserved or reduced, 2) is the structure of the LV normal or abnormal, and 3) are there other structural abnormalities such as valvular, pericardial, or right ventricular abnormalities that could account for the clinical presentation? This information should be quantified with a numerical estimate of EF, measurement of ventricular dimensions and/or volumes, measurement of wall thickness, and evaluation of chamber geometry and regional wall motion. Right ventricular size and systolic performance should be assessed. Atrial size should also be determined semiquantitatively and left atrial dimensions and/or volumes measured.

Noninvasive hemodynamic data acquired at the time of echocardiography are an important additional correlate for patients with preserved or reduced EF. Combined quantification of the mitral valve inflow pattern, pulmonary venous inflow pattern, and mitral annular velocity provides data about characteristics of LV filling and left atrial pressure. Evaluation of the tricuspid valve regurgitant gradient coupled with measurement of inferior vena caval dimension and its response during respiration provides an estimate of systolic pulmonary artery pressure and central venous pressure.

Stroke volume may be determined with combined dimension measurement and pulsed Doppler in the LV outflow tract. However, abnormalities can be present in any of these parameters in the absence of HF. No one of these necessarily correlates specifically with HF; however, a totally normal filling pattern argues against clinical HF.

From a clinical perspective, the disease is clinically asymptomatic in the compensatory and early decompensatory phases (completely asymptomatic in stage A and with structural heart disease but no signs and symptoms of HF in stage B, cf. the ACC/AHA practice guidelines). Outward signs of the disease (such as shortness of breath) do not appear until well into the decompensatory phase (i.e., stages C and D according to the ACC/AHA guidelines). Current diagnosis is based on the outward symptoms of patients in stages C and D.

Typically patients with heart failure receive a standard treatment with drugs that interact with specific mechanisms involved in heart failure. There are no diagnostic tests that reflect those specific mechanisms reliably and help the physician to choose the right drug (and dose) for the right patient (e.g., ACE inhibitor, AT II, β-blockers, etc).

Prior Diagnosis of Heart Failure with Markers

Early assessment of patients at risk for heart failure appears to be possible only by biochemical markers since the individual at risk of developing heart failure at that stage is still free of clinical HF symptoms. There are no established biochemical markers currently available for the reliable pre-symptomatic assessment of the disease. By the time the diagnosis HF is established nowadays, the disease is already well underway.

The natriuretic peptide family, especially the atrial natriuretic peptide family and the brain natriuretic peptide family have in recent years proven to be of significant value in the assessment of HF.

Heart Failure Prognosis and Need

At least partially due to the late diagnosis, 50% of patients with HF die within two years of diagnosis. The 5-year survival rate is less than 30%. There is a significant need for new biochemical markers aiding in the early diagnosis of heart failure.

An improvement in the early assessment of individuals at risk for heart failure, i.e., of individuals that are clinically asymptomatic for heart failure is warranted.

It has been established in recent years that B-type natriuretic peptide markers represent an excellent tool to monitor disease progression in patients with HF and to assess their risk of cardiovascular complications, like heart attack.

However, as for many other diagnostic areas a single marker is not sufficient.

Whereas a low value of NT-proBNP has a very high negative predictive value for ruling out HF or LVD, the positive predictive value for heart failure in the above and other studies (cf. Triepels R. H., et al., Clin. Chem. 49, Suppl. A (2003) 37-38) has been found to be in the range of 50-60%. Thus a marker useful in assessing individuals at risk for heart failure that on its own e.g., has a high, or in combination with NT-proBNP, and as compared to NT-proBNP alone has an improved positive predictive value for HF is of high clinical/practical importance.

A marker aiding in the assessment of a patient with heart failure also is of high importance to achieve further technical progress in this clinically very important and demanding diagnostic area.

SUMMARY OF THE INVENTION

It has now been found and established that the marker insulin like growth factor binding protein 7 (IGFBP-7) can aid in the assessment of heart failure. In one embodiment it can help to assess whether an individual is at risk of developing heart failure. In a further aspect it can aid in the assessment of disease progression. In another embodiment, it can aid in predicting the onset of heart failure. In another embodiment it can aid in assessing and selecting an appropriate treatment regimen to prevent or treat heart failure.

Disclosed herein is a method for assessing heart failure in an individual comprising the steps of measuring in a sample obtained from the individual the concentration of the marker IGFBP-7, of optionally measuring in the sample the concentration of one or more other marker(s) of heart failure, and of assessing heart failure by comparing the concentration of IGFBP-7 and optionally the concentration(s) of the one or more other marker to the concentration of this marker or these markers as established in a control sample.

The invention also relates to the use of protein IGFBP-7 as a marker molecule in the assessment of heart failure.

Further disclosed is the use of a marker combination comprising IGFBP-7 and one or more other marker of heart failure in the assessment of heart failure.

Also provided is a kit for performing the method for assessing heart failure in vitro comprising the steps of measuring in a sample the concentration of the marker IGFBP-7, of optionally measuring in the sample the concentration of one or more other marker(s) of heart failure, and of assessing heart failure by comparing the concentration of IGFBP-7 and optionally the concentration(s) of the one or more other marker to the concentration of this marker or these markers as established in a reference population, the kit comprising the reagents required to specifically measure IGFBP-7 and the optionally one or more other marker of heart failure.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
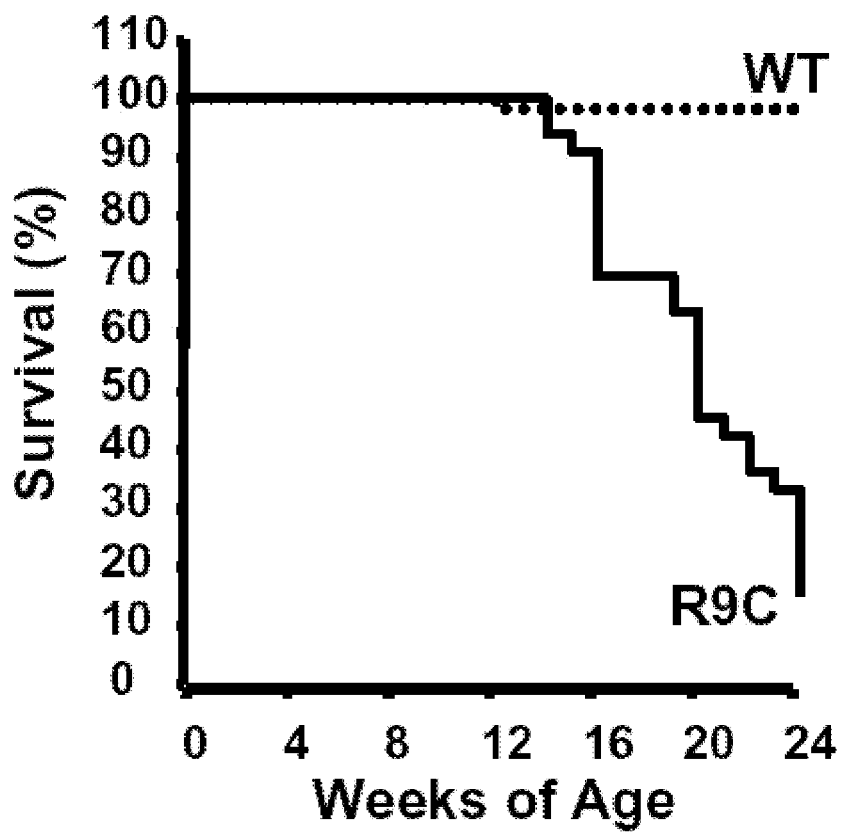
FIG. 1A: Phenotypic analyses of wildtype and R9C mice. (A) Survival curves for wildtype mice (n=79) and R9C mice (n=44) are generated following a 24 week period

In a first embodiment the present invention relates to a method for assessing heart failure in an individual comprising the steps of a) measuring in a sample obtained from the individual the concentration of the marker IGFBP-7, b) optionally measuring in the sample the concentration of one or more other marker(s) of heart failure, and c) assessing heart failure by comparing the concentration determined in step (a) and optionally the concentration(s) determined in step (b) to the concentration of this marker or these markers as established in a control sample.

As used herein, each of the following terms has the meaning associated with it in this section.

The articles "a" and "an" are used herein to refer to one or to more than one (i.e., to at least one) of the grammatical object of the article. By way of example, "an antibody" means one antibody or more than one antibody.

The expression "one or more" denotes 1 to 50, preferably 1 to 20 also preferred 2, 3, 4, 5, 6, 7, 8, 9, 10, 12, or 15.

The term "marker" or "biochemical marker" as used herein refers to a molecule to be used as a target for analyzing a patient's test sample. In one embodiment examples of such molecular targets are proteins or polypeptides. Proteins or polypeptides used as a marker in the present invention are contemplated to include naturally occurring fragments of said protein in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. In addition, or in the alternative a marker polypeptide may carry a post-translational modification. Examples of posttranslational modifications amongst others are glycosylation, acylation, and/or phosphorylation.

The term "assessing heart failure" is used to indicate that the method according to the present invention will aid the physician to assess whether an individual is at risk of developing heart failure, or aid the physician in his assessing of an HF patient in one or several other areas of diagnostic relevance in HF. Preferred areas of diagnostic relevance in assessing an individual with HF are the staging of heart failure, differential diagnosis of acute and chronic heart failure, judging the risk of disease progression, guidance for selecting an appropriate drug, monitoring of response to therapy, and the follow-up of HF patients.

A "marker of heart failure" in the sense of the present invention is a marker that if combined with the marker IGFBP-7 adds relevant information in the assessment of HF to the diagnostic question under investigation. The information is considered relevant or of additive value if at a given specificity the sensitivity, or if at a given sensitivity the specificity, respectively, for the assessment of HF can be improved by including said marker into a marker combination already comprising the marker IGFBP-7. Preferably the improvement in sensitivity or specificity, respectively, is statistically significant at a level of significance of $p=0.05$, 0.02, 0.01 or lower. Preferably, the one or more other marker of heart failure is selected from the group consisting of a natriuretic peptide marker, a cardiac troponin marker, and a marker of inflammation.

The term "sample" as used herein refers to a biological sample obtained for the purpose of evaluation in vitro. In the methods of the present invention, the sample or patient sample preferably may comprise any body fluid. Preferred test samples include blood, serum, plasma, urine, saliva, and synovial fluid. Preferred samples are whole blood, serum, plasma or synovial fluid, with plasma or serum representing the most convenient type of sample. As the skilled artisan will appreciate, any such assessment is made in vitro. The patient sample is discarded afterwards. The patient sample is solely used for the in vitro method of the invention and the material of the patient sample is not transferred back into the patient's body. Typically, the sample is a liquid sample, e.g., whole blood, serum, or plasma.

The expression "comparing the concentration . . . to the concentration as established in a control sample" is merely used to further illustrate what is obvious to the skilled artisan anyway. The control sample may be an internal or an external control sample. In one embodiment an internal control sample is used, i.e., the marker level(s) is(are) assessed in the test sample as well as in one or more other sample(s) taken from the same subject to determine if there are any changes in the level(s) of said marker(s). In another embodiment an external control sample is used. For an external control sample the presence or amount of a marker in a sample derived from the individual is compared to its presence or amount in an individual known to suffer from, or known to be at risk of, a given condition; or an individual known to be free of a given condition, i.e., "normal individual". For example, a marker level in a patient sample can be compared to a level known to be associated with a specific course of disease in HF. Usually the sample's marker level is directly or indirectly correlated with a diagnosis and the marker level is, e.g., used to determine whether an individual is at risk for HF. Alternatively, the sample's marker level can, e.g., be compared to a marker level known to be associated with a response to therapy in HF patients, the differential diagnosis of acute and chronic heart failure, the guidance for selecting an appropriate drug to treat HF, in judging the risk of disease progression, or in the follow-up of HF patients. Depending on the intended diagnostic use an appropriate control sample is chosen and a control or reference value for the marker established therein. It will be appreciated by the skilled artisan that such control sample in one embodiment is obtained from a reference population that is age-matched and free of confounding diseases. As also clear to the skilled artisan, the absolute marker values established in a control sample will be dependent on the assay used. Preferably samples from 100 well-characterized individuals from the appropriate reference population are used to establish a control (reference) value. Also preferred the reference population may be chosen to consist of 20, 30, 50, 200, 500 or 1000 individuals. Healthy individuals represent a preferred reference population for establishing a control value.

An increased value for IGFBP-7 as measured from a sample derived from an individual is indicative for heart failure.

The values for IGFBP-7 as measured in a control group or a control population are for example used to establish a cut-off value or a reference range. A value above such cut-off value or out-side the reference range and its higher end is considered as elevated.

In a one embodiment a fixed cut-off value is established. Such cut-off value is chosen to match the diagnostic question of interest.

In one embodiment values for IGFBP-7 as measured in a control group or a control population are used to establish a reference range. In a preferred embodiment an IGFBP-7 concentration is considered as elevated if the value measured is above the 90%-percentile of the reference range. In further preferred embodiments an IGFBP-7 concentration is considered as elevated if the value measured is above the 95%-percentile, the 96%-percentile, the 97%-percentile or the 97.5%-percentile of the reference range.

In one embodiment the control sample will be an internal control sample. In this embodiment serial samples are obtained from the individual under investigation and the marker levels are compared. This may for example be useful in assessing the efficacy of therapy.

The method according to the present invention is based on a liquid sample which is obtained from an individual and on the measurement of IGFBP-7 in such sample. An "individual" as used herein refers to a single human or non-human organism. Thus, the methods and compositions described herein are applicable to both human and veterinary disease. Preferably the individual is a human being.

IGFBP-7

Insulin-like Growth Factors (IGFs) and Corresponding Binding Proteins (BPs)

The Insulin like growth factor binding protein (IGFBP) system plays an important role in cell growth and differentiation. It comprises two ligands, IGF-I and IGF-II, two receptors, type 1 and type 2 IGF receptors, and as of 1995 six IGF-binding proteins (IGFBPs), IGFBP-1 to -6 (Jones, J. I., et al., Endocr. Rev. 16 (1995) 3-34). Recently the IGFBP family has been expanded to include the IGFBP-related proteins (IGFBP-rPs), which have significant structural similarities with the IGFBPs (Hwa, V., et al., Endocr. Rev 20 (1999) 761-787). Thus, the IGFBP superfamily includes the six conventional IGFBPs, which have high affinity for IGFs, and at least 10 IGFBP-rPs, which not only share the conserved amino-terminal domain of the IGFBPs but also show some degree of affinity for IGFs and insulin. The IGFBP-rPs are a group of cysteine-rich proteins that control diverse cellular functions, such as cellular growth, cell adhesion and migration, and synthesis of the extracellular matrix. In addition, these proteins might be involved in biological processes like tissue proliferation and differentiation, reproduction, angiogenesis, wound repair, inflammation, fibrosis, and tumorigenesis (Hwa, V., et al., Endocr. Rev 20 (1999) 761-787).

IGF binding protein 7 (=IGFBP-7) (SEQ ID NO: 1) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). In the literature this molecule has also been denominated as FSTL2; IBP 7; IGF binding protein related protein 1; IGFBP 7; IGFBP 7v; IGFBP rP1; IGFBP7; IGFBPRP1; insulin like growth factor binding protein 7; insulin like growth factor binding protein 7 precursor; MAC25; MAC25 protein; PGI2 stimulating factor; and PSF or Prostacyclin stimulating factor. Northern blot studies revealed a wide expression of this gene in human tissues, including heart, brain, placenta, liver, skeletal muscle, and pancreas (Oh, Y., et al., J. Biol. Chem. 271 (1996) 30322-30325).

IGFBP-7 was initially identified as a gene differentially expressed in normal leptomeningeal and mammary epithelial cells, compared with their counterpart tumor cells, and named meningioma-associated cDNA (MAC25) (Burger, A. M., et al., Oncogene 16 (1998) 2459-2467). The expressed protein was independently purified as a tumor derived adhesion factor (later renamed angiomodulin) (Sprenger, C. C., et al., Cancer Res 59 (1999) 2370-2375) and as a prostacyclin-stimulating factor (Akaogi, K., et al., Proc Natl Acad Sci USA 93 (1996) 8384-8389). It has additionally been reported as T1A12, a gene down-regulated in breast carcinomas (StCroix, B., et al., Science 289 (2000) 1197-1202).

The biological roles of IGFBP-7 have not yet been clearly established. Preliminary experimental data are somewhat controversial and relate to diverse actions for IGFBP-7, such as tumor suppression (Sprenger, C. C., et al., Cancer Res 59 (1999) 2370-2375), tumor growth promotion (Lopez-Bermejo, A., et al., J. Clinical Endocrinology and Metabolism 88 (2003) 3401-3408, stimulation of prostacyclin (Akaogi, K., et al., Proc. Natl. Acad. Sci. USA 93 (1996) 8384-8389) and involvement in angiogenesis (Yamauchi, T., et al., Biochem J. 303 (1994) 591-598) and senescence (Lopez-Bermejo, A., et al., Endocrinology 141 (2000) 4072-4080).

Differential expression of IGFBP-7 mRNA was measured in patients suffering from various diseases including cardiac disease, kidney disease, inflammatory diseases (U.S. Pat. No. 6,709,855 to Scios Inc.) and vascular graft disease (US2006/0,003,338).

A number of different assays has been described and used to test for the hormone binding properties of IGFBP-7. Low affinity IGF binding was analyzed via competitive affinity cross-linking assays. Recombinant human mac25 protein specifically binds IGF-I and-II (Oh, Y., et al., J. Biol. Chem. 271 (1996) 30322-20325; Kim, H. S., et al., Proc. Natl. Acad. Sci USA 94 (1997) 12981-12986.) IGFBP activity can also be detected by measuring the ability of the protein to bind radio-labeled IGF in Western ligand blotting.

Immunological determination of circulating IGFBP-7 was performed recently. Low levels of this analyte were detected in random human sera and increased serum levels have been seen in association with insulin-resistance (Lopez-Bermejo, A., et al., J. Clinical Endocrinology and Metabolism 88 (2003) 3401-3408, Lopez-Bermejo, A., et al., Diabetes 55 (2006) 2333-2339).

Several patent applications deal with the potential utility of IGFBPs as diagnostic agents, preventive agents and therapeutic agents for a broad variety of diseases.

US2003/0186308 discloses a human polypeptide called Prostacyclin-Stimulating Factor-2 (PSF-2; =IGFBP-7) and its optional diagnostic application to detect a pathological condition.

WO 2003/54004 speculates that IGFBP-7 may be used for diagnosis of a large variety of diseases. It is alleged that it may be used to diagnose a cell proliferative disorder, an autoimmune/inflammatory disorder, a cardiovascular disorder, a neurological disorder, a developmental disorder, a metabolic disorder, a reproductive disorder, an infection, a growth disorder such as growth hormone deficiency, acromegaly, IUGR, macrosomia, tumorigenesis and cancer (e.g., breast cancer), diabetes and its complications (e.g., diabetic kidney disease), chronic renal failure, vascular disease, asthma, atherosclerosis and restenosis and other pathological conditions.

US2004/0072238 relates to the detection of differentially expressed or mutated Insulin like growth factor binding proteins for diagnosis of: diseases accompanying abnormal cell growth, diseases accompanying angiopathy, diseases accompanying abnormal bone metabolism, diseases accompanying disorders of insulin-like growth factors or growth hormone action, diseases accompanying abnormal differentiation or growth of smooth muscle cells, diseases accompanying abnormal differentiation or growth of skeletal muscle cells, diseases accompanying abnormal gastric acid secretion, and inflammatory diseases. Almost any medically relevant condition is then mentioned in a further list said to be comprised in one of the diseases accompanying one or the other disorder as mentioned before.

WO 2004/042000 describes the therapeutic application of more than 150 secreted proteins for various medical indications. One of the sequences mentioned is the sequence of IGFBP-7.

WO 1994/029448 describes the use of a PGI2 production promoting protein (PGI2 stimulating factor) for therapy of several diseases like hemolytic uremic syndrome, thrombotic thrombocytopenic purpura, peripheral embolism, cardiac ischemia, cerebral ischemia, arteriosclerosis, cerebral infarction, hyperlipemia, diabetes, cardiac failure, angina pectoris, ischemic heart disease, congestive heart disease, choroidal circulatory disturbance, bronchial disease, gastric ulcer and eclampsia of pregnancy on the basis of the platelet aggregation inhibitor activity, smooth muscle relaxant activity and gastric secretion.

Preferably the marker IGFBP-7 is specifically measured from a liquid sample by use of a specific binding agent.

A specific binding agent is, e.g., a receptor for IGFBP-7, a lectin binding to IGFBP-7 or an antibody to IGFBP-7. A specific binding agent has at least an affinity of $10^7$ l/mol for its corresponding target molecule. The specific binding agent preferably has an affinity of $10^8$ l/mol or even more preferred of $10^9$ l/mol for its target molecule. As the skilled artisan will appreciate the term specific is used to indicate that other biomolecules present in the sample do not significantly bind to the binding agent specific for IGFBP-7. Preferably, the level of binding to a biomolecule other than the target molecule results in a binding affinity which is only 10% or less, more preferably only 5% or less of the affinity to the target molecule, respectively. A preferred specific binding agent will fulfill both the above minimum criteria for affinity as well as for specificity.

A specific binding agent preferably is an antibody reactive with IGFBP-7. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, Elsevier Science Publishers B.V., Amsterdam (1990), the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in goats may be used. However, clearly also polyclonal antibodies from different species, e.g., rats, rabbits or guinea pigs, as well as monoclonal antibodies can be used. Since monoclonal antibodies can be produced in any amount required with constant properties, they represent ideal tools in development of an assay for clinical routine.

The generation and the use of monoclonal antibodies to IGFBP-7 in a method according to the present invention, respectively, represent yet other preferred embodiments.

It is not easy to purify IGFBP-7 from a natural source. The recombinant production of IGFBP-7 is a method of choice to obtain higher amounts of IGFBP-7. In a preferred embodiment IGFBP-7 is produced by recombinant expression using an eukaryotic expression system. Examples of eukaryotic expression systems are baculovirus expression, expression in yeast and expression in a mammalian expression system. In one preferred embodiment the expression of IGFBP-7 will be performed in a mammalian expression system. Examples of mammalian expression systems are CHO cells, HEK cells, myeloma cells, etc. In a further preferred embodiment the recombinantly produced IGFBP-7 is used as an antigen in the production of poly- or monoclonal antibodies against IGFBP-7. It may be also preferable to purify polyclonal antibodies by immunoadsorption over an IGFBP-7 immunoadsorber make use of a recombinantly produced IGFBP-7 as described herein above.

As the skilled artisan will appreciate now, that IGFBP-7 has been identified as a marker which is useful in the assessment of HF, alternative ways may be used to reach a result comparable to the achievements of the present invention. For example, alternative strategies to generate antibodies may be used. Such strategies comprise amongst others the use of synthetic or recombinant peptides, representing a clinically relevant epitope of IGFBP-7 for immunization. Alternatively, DNA immunization also known as DNA vaccination may be used.

For measurement the liquid sample obtained from an individual is incubated with the specific binding agent for IGFBP-7 under conditions appropriate for formation of a binding agent IGFBP-7-complex. Such conditions need not be specified, since the skilled artisan without any inventive effort can easily identify such appropriate incubation conditions. The amount of binding agent IGFBP-7-complex is measured and used in the assessment of HF. As the skilled artisan will appreciate there are numerous methods to measure the amount of the specific binding agent IGFBP-7-complex all described in detail in relevant textbooks (cf., e.g., Tijssen P., supra, or Diamandis, E. P. and Christopoulos, T. K. (eds.), Immunoassay, Academic Press, Boston (1996)).

Preferably IGFBP-7 is detected in a sandwich type assay format. In such assay a first specific binding agent is used to capture IGFBP-7 on the one side and a second specific binding agent, which is labeled to be directly or indirectly detectable, is used on the other side. Preferably, an antibody to IGFBP-7 is used in a qualitative (IGFBP-7 present or absent) or quantitative (amount of IGFBP-7 is determined) immunoassay.

As described in detail in the Examples section, two mouse models have been used to identify polypeptides found in heart tissue of experimental animals by advanced proteomics methods. However these models did yield at least partially conflicting data, and, of course tissue data for polypeptides are not representative to the presence or absence of these polypeptides in the circulation. A marker found to be differentially expressed in one model may not be differentially expressed in a second model or even show conflicting data in yet a further model. Even if a protein may be differentially expressed in tissue this protein in most cases is not of any diagnostic relevance if measured from a bodily fluid, because it may not be released to the circulation, may become fragmented or modified, e.g., upon release from a cell or tissue, may not be stable in the circulation, may not be measurable in the circulation, may not be specific for a given disease, etc.

The inventors of the present invention surprisingly are able to detect protein IGFBP-7 in a bodily fluid sample. Even more surprising they are able to demonstrate that the presence of IGFBP-7 in such liquid sample obtained from an individual can be correlated to HF. No tissue and no biopsy sample is required to make use of the marker IGFBP-7 in the assessment of HF. Measuring the level of protein IGFBP-7 is considered very advantageous in the field of HF.

In a preferred embodiment the method according to the present invention is practiced with serum as liquid sample material. In a further preferred embodiment the method according to the present invention is practiced with plasma as liquid sample material. In a further preferred embodiment the method according to the present invention is practiced with whole blood as liquid sample material.

In a further preferred embodiment, the present invention relates to use of protein IGFBP-7 as a marker molecule in the assessment of heart failure from a liquid sample obtained from an individual.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case of HF. As the skilled artisan will appreciate, no biochemical marker in the field of HF is diagnostic with 100% specificity and at the same time 100% sensitivity for a certain diagnostic question. Rather, biochemical markers are used to assess with a certain likelihood or predictive value an underlying diagnostic question. The skilled artisan is fully familiar with the mathematical/statistical methods that routinely are used to calculate a relative risk or likelihood for the diagnostic question to be assessed. In routine clinical practice various clinical symptoms and biological markers are generally considered together by a physician in the diagnosis, treatment, and management of the underlying disease.

Preferably in a further preferred embodiment of the present invention the method for assessment of HF is performed by measuring the concentration of IGFBP-7 and of one or more other marker and by using the concentration of IGFBP-7 and of the one or more other marker in the assessment of HF.

In the assessment of HF the marker IGFBP-7 will aid the physician in one or more of the following aspects: to assess an individual's risk for heart failure or to assess a patient having heart failure, e.g., with the intention to identify the stage of heart failure, to differentiate between acute and chronic heart failure, to judge the risk of disease progression, to provide guidance in selecting an appropriate therapy, to monitor a patient's response to therapy, and to monitor the course of disease, i.e., in the follow-up of HF patients.

Screening (Assessment Whether Individuals are at Risk for Developing Heart Failure):

In a preferred embodiment the present invention relates to an in vitro method for assessing whether an individual is at risk for developing heart failure comprising the steps of measuring in a sample the concentration of the marker IGFBP-7, of optionally measuring in the sample the concentration of one or more other marker(s) of heart failure, and of assessing said individual's risk for developing heart failure by comparing the concentration for IGFBP-7 and optionally the concentration(s) determined for the optionally one or more other marker(s) to the concentration of this marker or these markers to its or their reference value(s).

Screening in the sense of the present invention relates to the unbiased assessment of individuals regarding their risk for developing heart failure. Whereas such screening may in theory be performed on any sample, in clinical practice such screening option will usually be given to individuals somehow at risk for development of heart failure. As discussed above, such individuals may clinically be asymptomatic, i.e., they have no signs or symptoms of HF. In one preferred embodiment screening for HF will be given to individuals at risk of developing heart failure, e.g., falling into the stages A or B as defined by the ACC/AHA practice guidelines.

As mentioned above, heart failure is one of the most prevalent, costly and life-threatening diseases in developed countries. Because of its high prevalence and its long asymptomatic phase identification of individuals at risk for developing HF would be of utmost importance to intervene in and if possible to interrupt the course of disease. Without a very early risk assessment, prevention of disease progression from the asymptomatic state into a symptomatic phase of HF appears impossible.

The risk for heart failure is assessed by mathematical/statistical methods fully known and understood by the skilled artisan. Preferably an individual's risk for heart failure is expressed in relative terms and given as the so-called relative risk (=RR). In order to calculate such RR for heart failure an individual's value for IGFBP-7 is compared to the values established for IGFBP-7 in a reference population, preferably healthy individuals not developing heart failure. Also preferred the assessment of such RR for heart failure is based on a group of individuals that have developed heart failure within the study period, preferably within one or also preferred within two years, and a group of individuals that did not develop heart failure in the same study period.

In another preferred embodiment the present invention relates to the use of the marker IGFBP-7 in the screening for heart failure. As the skilled artisan knows the term "use as a marker" implies that the concentration of a marker molecule is quantified by appropriate means and that value measured for such marker is then used to indicate, i.e., to mark, the presence or absence of a disease or clinical condition. Appropriate means for quantitation for example are specific binding agents, like antibodies.

Preferably the screening for HF will be performed in individuals suspected to be at risk of future heart failure. Patients at risk of future heart failure in this sense are patients diagnosed with hypertension, atherosclerotic disease, diabetes, obesity and metabolic syndrome. Preferably the risk for future heart failure is assessed with individuals suffering from hypertension, atherosclerotic disease, diabetes, and/or metabolic syndrome.

Also preferred is the use of the marker IGFBP-7 in assessing the risk for future heart failure for an individual in stage B according to the ACC/AHA practice guidelines, i.e., an individual exhibiting a structural change at the heart but not showing symptoms of heart failure.

In a further preferred embodiment the present invention relates to the use of IGFBP-7 as one marker of a HF marker combination for HF screening purposes.

In the screening setting an elevated level of IGFBP-7 is a positive indicator for an individual's increased risk to develop heart failure.

Staging of Patients

In a preferred embodiment the present invention relates to an in vitro method aiding in the staging of heart failure patients, comprising the steps of a) measuring in a sample the concentration of the marker IGFBP-7, of b) optionally measuring in the sample the concentration of one or more other marker(s) of heart failure, and staging heart failure by comparing the concentration determined in step (a) and optionally the concentration(s) determined in step (b) to the concentration of this marker or these markers to its or their reference value(s). Preferably the level of marker IGFBP-7 is used as an aid in classifying the individuals investigated into the groups of individuals that are clinically "normal" (i.e., individuals in stage A according to the ACA/ACC classification), asymptomatic patients having structural heart disease (stage B according to the ACA/ACC classification) and the group of patients having heart failure (i.e., patients in stage C or stage D according to the ACA/ACC classification).

Differentiation Between an Acute Cardiac Event and Chronic Cardiac Disease

In a preferred embodiment the present invention relates to an in vitro method aiding in the differential diagnosis between an acute cardiac event and chronic cardiac disease, comprising the steps of measuring in a sample the concentration of the marker IGFBP-7, of optionally measuring in the sample the concentration of one or more other marker(s) of heart failure, and establishing a differential diagnosis between an acute cardiac event and chronic cardiac disease by comparing the concentration determined in step (a) and optionally the concentration(s) determined in step (b) to the concentration of this marker or these markers to its or their reference value(s).

The person skilled in the art is familiar with the meanings of "acute cardiac event" and of "chronic cardiac disease".

Preferably, an "acute cardiac event" relates to an acute condition, disease or malfunction of the heart, particularly to acute heart failure, e.g., myocardial infarction (MI) or arrhythmia. Depending on the extent of an MI, it may be followed by LVD and CHF.

Preferably, a "chronic cardiac disease" is a weakening of heart function, e.g., due to ischemia of the heart, coronary artery disease, or previous, particularly small, myocardial infarction(s) (possibly followed by progressing LVD). It may also be a weakening due to inflammatory diseases, heart valve defects (e.g., mitral valve defects), dilatative cardiomyopathy, hypertrophic cardiomyopathy, heart rhythm defects (arrhythmias), and chronic obstructive pulmonary disease. Thus, it is clear that a chronic cardiac disease may also include patients who had suffered from an acute coronary syndrome, e.g., MI, but who are presently not suffering from an acute cardiac event.

It is important to differentiate between an acute cardiac event and chronic cardiac disease, because an acute cardiac event and chronic cardiac disease may require quite different treatment regimens. For example, for a patient presenting with acute myocardial infarction early treatment for reperfusion may be of utmost importance. Whereas a treatment for reperfusion performed on a patient with chronic heart failure at best is of no or only little harm to this patient.

In a further preferred embodiment according to the present invention the marker IGFBP-7 is used in the differential diagnosis of acute and chronic heart failure.

Assessing the Risk of Disease Progression

In a preferred embodiment the present invention relates to an in vitro method for assessing an HF-patient's risk for disease progression, comprising the steps of measuring in a sample the concentration of the marker IGFBP-7, of optionally measuring in the sample the concentration of one or more other marker(s) of heart failure, and of establishing said individual's risk for disease progression by comparing the concentration for IGFBP-7 and optionally the concentration(s) determined for the optionally one or more other marker(s) to the concentration of this marker or these markers to its or their reference value(s).

At present it is very difficult to assess or to even predict with a reasonable likelihood whether a patient diagnosed with HF has a more or less stable status or whether the disease will progress and the patient's health status as result is likely to worsen. Severity and progression of heart failure is clinically usually established by assessing the clinical symptoms or by identification of adverse changes by using imaging technologies such as echocardiography. In one embodiment the worsening of heart failure is established by monitoring the left ventricular ejection fraction (LVEF). A deterioration in LVEF by 5% or more is considered as disease progression.

In a further preferred embodiment the present invention therefore relates to the use of the marker IGFBP-7 in assessing the risk of disease progression for a patient suffering from HF. In the assessment of disease progression for patients suffering from HF an elevated level of IGFBP-7 is an indicator for an increased risk of disease progression.

Guidance in Selecting an Appropriate HF Therapy

In a preferred embodiment the present invention relates to an in vitro method, aiding in the selection of an appropriate HF-therapy, comprising the steps of measuring in a sample the concentration of the marker IGFBP-7, of optionally measuring in the sample the concentration of one or more other marker(s) of heart failure, and of selecting an appropriate therapy by comparing the concentration for IGFBP-7 and optionally the concentration(s) determined for the optionally one or more other marker(s) to the concentration of this marker or these markers to its or their reference value(s).

It is expected that the marker IGFBP-7 will be of help in aiding the physician to select the most appropriate treatment regimen from the various treatment regimens at hand in the area of heart failure. In a further preferred embodiment therefore relates to the use of the marker IGFBP-7 in selecting a treatment regimen for a patient suffering from HF.

Monitor a Patient's Response to Therapy

In a preferred embodiment the present invention relates to an in vitro method for monitoring a patient's response to HF-therapy, comprising the steps of a) measuring in a sample the concentration of the marker IGFBP-7, of b) optionally measuring in the sample the concentration of one or more other marker(s) of heart failure, and of monitoring a patient's response to HF-therapy by comparing the concentration determined in step (a) and optionally the concentration(s) determined in step (b) to the concentration of this marker or these markers to its or their reference value(s).

Alternatively the above method for motoring a patient's response to therapy can be practiced by establishing the pre- and post-therapeutic marker level for IGFBP-7 and for the optionally one or more other marker and by comparing the pre- and the post-therapeutic marker level(s).

The diagnosis of heart failure is clinically established. According to the present invention HF is considered clinically established if a patient meets the criteria of stages C or D as defined by the ACC/AHA practice guidelines. According to these guidelines stage C refers to patients with structural heart disease and with prior or current symptoms of heart failure. Patients in stage D are those patients with refractory heart failure that require specialized interventions.

As indicated further above the values measured for NT-proBNP are highly correlated to the severity of heart failure. However, both BNP and NT-proBNP appear to be not ideal in monitoring a patient's response to therapy, cf. e.g., Beck-da-Silva, L., et al., Congest. Heart Fail. 11 (2005) 248-253, quiz 254-255.

The marker IGFBP-7 appears to be appropriate to monitor a patient's response to therapy. The present invention thus also relates to the use of IGFBP-7 in monitoring a patient's response to therapy. In that diagnostic area the marker IGFBP-7 can also be used for establishing a baseline value before therapy and to measure IGFBP-7 at one time-point or several time-points after therapy. In the follow-up of HF patients an elevated level of IGFBP-7 is a positive indicator for an effective treatment of HF.

Marker Combination

Biochemical markers can either be determined individually or, in a preferred embodiment of the invention, they can be measured simultaneously using a chip- or a bead-based array technology. The concentrations of the biomarkers are then interpreted independently using an individual cut-off for each marker or they are combined for interpretation, i.e., they form a marker combination.

As the skilled artisan will appreciate the step of correlating a marker level to a certain likelihood or risk can be performed and achieved in different ways. Preferably the values measured for the marker IGFBP-7 and the one or more other marker(s) are mathematically combined and the combined value is correlated to the underlying diagnostic question. Marker values may be combined with the measurement of IGFBP-7 by any appropriate state of the art mathematical method.

Preferably the mathematical algorithm applied in the combination of markers is a logistic function. The result of applying such mathematical algorithm or such logistical function preferably is a single value. Dependent on the underlying diagnostic question such value can easily be correlated to e.g., the risk of an individual for heart failure or to other intended diagnostic uses helpful in the assessment of patients with HF. In a preferred way such logistic function is obtained by a) classification of individuals into the groups, e.g., into normals, individuals at risk for heart failure, patients with acute or chronic heart failure and so on, b) identification of markers which differ significantly between these groups by univariate analysis, c) logistic regression analysis to assess the independent discriminative values of markers useful in assessing these different groups and d) construction of the logistic function to combine the independent discriminative values. In this type of analysis the markers are no longer independent but represent a marker combination.

In a preferred embodiment the logistic function used for combining the values for IGFBP-7 and the value of at least one further marker is obtained by a) classification of individuals into the groups of normals and individuals at risk of heart failure, respectively, b) establishing the values for IGFBP-7 and the value of the at least one further marker c) performing logistic regression analysis and d) construction of the logistic function to combine the marker values for IGFBP-7 and the value of the at least one further marker.

A logistic function for correlating a marker combination to a disease preferably employs an algorithm developed and obtained by applying statistical methods. Appropriate statistical methods, e.g., are Discriminant analysis (DA) (i.e., linear-, quadratic-, regularized-DA), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting/Bagging Methods), Generalized Linear Models (i.e., Logistic Regression), Principal Components based Methods (i.e., SIMCA), Generalized Additive Models, Fuzzy Logic based Methods, Neural Networks and Genetic Algorithms based Methods. The skilled artisan will have no problem in selecting an appropriate statistical method to evaluate a marker combination of the present invention and thereby to obtain an appropriate mathematical algorithm. Preferably the statistical method employed to obtain the mathematical algorithm used in the assessment of heart failure is selected from DA (i.e., Linear-, Quadratic-, Regularized Discriminant Analysis), Kernel Methods (i.e., SVM), Nonparametric Methods (i.e., k-Nearest-Neighbor Classifiers), PLS (Partial Least Squares), Tree-Based Methods (i.e., Logic Regression, CART, Random Forest Methods, Boosting Methods), or Generalized Linear Models (i.e., Logistic Regression). Details relating to these statistical methods are found in the following references: Ruczinski, I., et al., J. of Computational and Graphical Statistics 12 (2003) 475-511; Friedman, J. H., J. of the American Statistical Association 84 (1989) 165-175; Hastie, T., et al., The Elements of Statistical Learning, Springer Verlag (2001); Breiman, L., et al. Classification and regression trees, Wadsworth International Group, California (1984); Breiman, L., Machine Learning 45 (2001) 5-32; Pepe, M. S., The Statistical Evaluation of Medical Tests for Classification and Prediction, Oxford Statistical Science Series, 28, Oxford University Press (2003); and Duda, R. O., et al., Pattern Classification, John Wiley & Sons, Inc., 2nd ed. (2001).

It is a preferred embodiment of the invention to use an optimized multivariate cut-off for the underlying combination of biological markers and to discriminate state A from state B, e.g., normals and individuals at risk for heart failure, HF patients responsive to therapy and therapy failures, patients having an acute heart failure and HF patients having chronic heart failure, HF patients showing disease progression and HF patients not showing disease progression, respectively.

The area and the receiver operator curve (=AUC) is an indicator of the performance or accuracy of a diagnostic procedure. Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example, health and disease or disease progression versus no disease progression.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/ (number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot (AUC). By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

The overall assay sensitivity will depend on the specificity required for practicing the method disclosed here. In certain preferred settings a specificity of 75% may be sufficient and statistical methods and resulting algorithms can be based on this specificity requirement. In one preferred embodiment the method used to assess individuals at risk for heart failure is based on a specificity of 80%, of 85%, or also preferred of 90% or of 95%.

As discussed above, the marker IGFBP-7 aids in assessing an individuals risk of developing heart failure as well as in the further in vitro diagnostic assessment of a patient having heart failure. A preferred embodiment accordingly is the use of IGFBP-7 as a marker molecule in the assessment of heart failure.

The use of a marker combination comprising IGFBP-7 and one or more other marker(s) of HF in the assessment of HF patients or in the assessment of individuals at risk for HF represents a further preferred embodiment of the present invention. In such marker combination the one or more other marker(s) preferably is selected from the group consisting of a natriuretic peptide marker, a cardiac troponin marker, and a marker of inflammation.

The one or more preferred selected other HF marker(s) with which the measurement of IGFBP-7 may be combined preferably is or are selected from the group consisting of a natriuretic peptide marker, a cardiac troponin marker, and a marker of inflammation. These preferred other markers whose measurement(s) preferably are combined with the measurement of IGFBP-7 or which form part of the HF marker combination comprising IGFBP-7, respectively, are discussed in more detail below.

Natriuretic Peptide Marker

A natriuretic peptide marker in the sense of the present invention is either a marker selected from the atrial natriuretic peptide (ANP) family or a marker selected from the brain natriuretic peptide (BNP) family.

The polypeptide markers in either the atrial natriuretic peptide family or in the brain natriuretic peptide family are derived from the preproforms of the corresponding active hormones.

Preferred natriuretic peptide markers according to the present invention are NT-proANP, ANP, NT-proBNP, BNP, and immunologically detectable physiological fragments thereof. As the skilled artisan readily appreciates, the immunologically detectable fragment has to comprise at least one epitope allowing for the specific detection of such physiological fragment. A physiological fragment is a fragment as naturally present in an individual's circulation.

The markers in both the natriuretic peptide families represent fragments of the corresponding pro-hormones, i.e., proANP and proBNP, respectively. Since similar considerations apply for both families, only the BNP marker family shall be described in some detail. The pro-hormone of the BNP family, i.e., proBNP consists of 108 amino acids. proBNP is cleaved into the 32 C-terminal amino acids (77-108) representing the biologically active hormone BNP and the N-terminal amino acids 1-76 called N-terminal proBNP (or NT-proBNP). BNP, N-terminal proBNP (1-76) as well as further breakdown products (Hunt, P. J., et al., Biochem. Biophys. Res. Com. 214 (1995) 1175-1183) circulate in blood. Whether the complete precursor molecule (proBNP 1-108) also occurs in the plasma is not completely resolved. It is however described (Hunt, P. J., et al., Peptides 18 (1997) 1475-1481) that a low release of proBNP (1-108) in plasma is detectable but that due to the very quick partial breakdown at the N-terminal end some amino acids are absent. Today it is generally accepted that e.g., for NT-proBNP the central portion of the molecule, residing in between the amino acids 10 to 50 represents a physiologically rather stable part. NT-proBNP molecules comprising this central part of NT-proBNP can be reliably measured from bodily fluids. Detailed disclosure relating to methods based on the immunological detection of this central part of the NT-proBNP molecule is given in WO 00/45176 and the reader is referred thereto for details. It may be of further advantage to measure only a certain subfraction of NT-proBNP for which the term native NT-proBNP has been proposed. Detailed disclosure relating to this subfraction of NT-proBNP is found in WO 2004/099253. The artisan will find all necessary instructions there. Preferably the NT-proBNP measured is or corresponds to the NT-proBNP as measured with the ELECSYS (Roche Diagnostics GmbH) NT-proBNP assay from Roche Diagnostics, Germany.

Preanalytics are robust with NT-proBNP, which allows easy transportation of the sample to a central laboratory (Mueller, T., et al., Clin. Chem. Lab. Med. 42 (2004) 942-944). Blood samples can be stored at room temperature for several days or may be mailed or shipped without recovery loss. In contrast, storage of BNP for 48 hours at room temperature or at 4° Celsius leads to a concentration loss of at least 20% (Mueller, T., et al., supra; Wu, A. H., et al., Clin. Chem. 50 (2004) 867-873).

The brain-derived natriuretic peptide family (especially BNP and NT-proBNP) has been thoroughly investigated in the screening of certain populations for HF. The findings with these markers, especially with NT-proBNP are quite encouraging. Elevated values of NT-proBNP even in asymptomatic "patients" are clearly indicative for "heart problems" (Gremmler, B., et al., Exp. Clin. Cardiol. 8 (2003) 91-94). These authors showed that an elevated NT-proBNP indicates the presence of 'cardio-renal distress' and should prompt referral for further investigation. In line with several other groups of investigators Gremmler, et al., also find that an abnormal NT-proBNP concentration is an accurate diagnostic test both for the exclusion of HF in the population and in ruling out left ventricular dysfunction (=LVD) in breathless subjects. The role of negative BNP or NT-proBNP values in ruling out HF or LVD is corroborated by other groups of investigators, cf., e.g., McDonagh, T. A., et al., Eur. J. Heart Fail. 6 (2004) 269-273; and Gustafsson, F., et al., J. Card. Fail. 11, Suppl. 5 (2005) S15-20.

BNP is produced predominantly (albeit not exclusively) in the ventricle and is released upon increase of wall tension. Thus, an increase of released BNP reflects predominantly dysfunctions of the ventricle or dysfunctions which originate in the atria but affect the ventricle, e.g., through impaired inflow or blood volume overload. In contrast to BNP, ANP is produced and released predominantly from the atrium. The level of ANP may therefore predominantly reflect atrial function.

ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min (Smith, M. W., et al., J. Endocrinol. 167 (2000) 239-246).

Therefore, depending on the time-course or properties of interest, either measurement of the active or the inactive forms of the natriuretic peptide can be advantageous.

In the assessment of an individual at risk for heart failure the value measured for IGFBP-7 is preferably combined with the value for NT-proANP and/or NT-proBNP. Preferably the value for NT-proBNP is combined with the value for IGFBP-7. Similar considerations apply for selecting an appropriate therapy, judging the risk of disease progression, and to monitoring the course of disease.

In case IGFBP-7 is used in assessing a patient's response to therapy its measurement is preferably combined with the measurement of ANP or BNP.

In case IGFBP-7 is used to differentiate between acute and chronic heart failure the preferred marker combination comprises IGFBP-7, ANP or proANP and BNP or proBNP.

Cardiac Troponin Marker

The term cardiac troponin relates to the cardiac isoforms of troponin I and troponin T. As already indicated above the term marker also relates to physiological variants of the marker molecule, like physiological fragments or complexes. For the cardiac troponin markers their physiologically occurring complexes are known to be of diagnostic relevance and are herewith expressly included.

Troponin T has a molecular weight of about 37.000 Da. The troponin T isoform that is found in cardiac tissue (cTnT) is sufficiently divergent from skeletal muscle TnT to allow for the production of antibodies that distinguish both these TnT isoforms. TnT is considered a marker of acute myocardial damage; cf. Katus, H. A., et al., J. Mol. Cell. Cardiol. 21 (1989) 1349-1353; Hamm, C. W., et al., N. Engl. J. Med. 327 (1992) 146-150; Ohman, E. M., et al., N. Engl. J. Med. 335 (1996) 1333-1341; Christenson, R. H., et al., Clin. Chem. 44 (1998) 494-501; and EP 0 394 819.

Troponin I (TnI) is a 25 kDa inhibitory element of the troponin complex, found in muscle tissue. TnI binds to actin in the absence of $Ca^{2+}$, inhibiting the ATPase activity of actomyosin. The TnT isoform that is found in cardiac tissue (cTnI) is 40% divergent from skeletal muscle TnI, allowing both isoforms to be immunologically distinguished. The normal plasma concentration of cTnI is <0.1 ng/ml (4 pM). cTnI is released into the bloodstream following cardiac cell death; thus, the plasma cTnI concentration is elevated in patients with acute myocardial infarction (Benamer, H., et al., Am. J. Cardiol. 82 (1998) 845-850).

The unique cardiac isoforms of troponin I and T allow them to be distinguished immunologically from the other troponins of skeletal muscle. Therefore, the release into the blood of troponin I and T from damaged heart muscle can be specifically related to damage of cardiac tissue. It is nowadays also appreciated by the skilled artisan that the cardiac troponins may be detected from the circulation either in their free form or as a part of a complex (cf. e.g., U.S. Pat. Nos. 6,333,397, 6,376,206 and 6,174,686).

In the assessment of an individual at risk for heart failure as well as in the assessment of a patient suffering from heart failure, the value measured for IGFBP-7 is preferably combined with the value for cardiac isoform of troponin T and/or troponin I. A preferred cardiac troponin used in combination with the marker IGFBP-7 is cardiac troponin T.

Marker of Inflammation

The skilled artisan is familiar with the term marker of inflammation. Preferred markers of inflammation are interleukin-6, C-reactive protein, serum amyloid A and a S100 protein.

Interleukin-6 (IL-6) is a 21 kDa secreted protein that has numerous biological activities that can be divided into those involved in hematopoiesis and into those involved in the activation of the innate immune response. IL-6 is an acute-phase reactant and stimulates the synthesis of a variety of proteins, including adhesion molecules. Its major function is to mediate the acute phase production of hepatic proteins, and its synthesis is induced by the cytokines IL-1 and TNF-α. IL-6 is normally produced by macrophages and T lymphocytes. The normal serum concentration of IL-6 is <5 pg/ml.

C-reactive protein (CRP) is a homopentameric $Ca^{2+}$-binding acute phase protein with 21 kDa subunits that is involved in host defense. CRP synthesis is induced by IL-6, and indirectly by IL-1, since IL-1 can trigger the synthesis of IL-6 by Kupffer cells in the hepatic sinusoids. The normal plasma concentration of CRP is <3 μg/ml (30 nM) in 90% of the healthy population, and <10 μg/ml (100 nM) in 99% of healthy individuals. Plasma CRP concentrations can, e.g., be measured by Serum amyloid A (=SAA) is an acute phase protein of low molecular weight of 11.7 kDa. It is predominantly synthesized by the liver in response to IL-1, IL-6 or TNF-α stimulation and is involved in the regulation of the T-cell dependent immune response. Upon acute events the concentration of SAA increases up to 1000-fold reaching one milligram per milliliter. It is used to monitor inflammation in diseases as divers as cystic fibrosis, renal graft refection, trauma or infections. In rheumatoid arthritis is has in certain cases been used as a substitute for CRP, but, SAA is not yet as widely accepted.

S100-proteins form a constantly increasing family of $Ca^{2+}$-binding proteins that today includes more than 20 members. The physiologically relevant structure of S100-proteins is a homodimer but some can also form heterodimers with each other, e.g., S100A8 and S100A9. The intracellular functions range from regulation of protein phosphorylation, of enzyme activities, or of the dynamics of the cytoskeleton to involvement in cell proliferation and differentiation. As some S100-proteins are also released from cells, extracellular functions have been described as well, e.g., neuronal survival, astrocyte proliferation, induction of apoptosis and regulation of inflammatory processes. S100A8, S100A9, the heterodimer S100A8/A9 and S100A12 have been found in inflammation with S100A8 responding to chronic inflammation, while S100A9, S100A8/A9 and S100A12 are increased in acute inflammation. S100A8, S100A9, S100A8/A9 and S100A12 have been linked to different diseases with inflammatory components including some cancers, renal allocraft rejection, colitis and most importantly to RA (Burmeister, G., and Gallacchi, G., Inflammopharmacology 3 (1995) 221-230; Foell, D., et al., Rheumathology 42 (2003) 1383-1389). The most preferred 5100 markers for assessing an individual at risk for HF or a patient having HF e.g., for use in a marker combination according to the present invention are S100A8, S100A9, S100A8/A9 heterodimer and S100A12.

sE-selectin (soluble endothelial leukocyte adhesion molecule-1, ELAM-1) is a 115 kDa, type-I transmembrane glycoprotein expressed only on endothelial cells and only after activation by inflammatory cytokines (IL-1β, TNF-α) or endotoxin. Cell-surface E-selectin is a mediator of the rolling attachment of leucocytes to the endothelium, an essential step in extravasion of leucocytes at the site of inflammation, thereby playing an important role in localized inflammatory response. Soluble E-selectin is found in the blood of healthy individuals, probably arising from proteolytic cleavage of the surface-expressed molecule. Elevated levels of sE-selectin in serum have been reported in a variety of pathological conditions (Gearing, A. J. and Hemingway, I., Ann. N.Y. Acad. Sci. 667 (1992) 324-331).

In a preferred embodiment the present invention relates to the use of IGFBP-7 as a marker molecule for HF in combination with one or more marker molecule(s) for HF in the assessment of HF from a liquid sample obtained from an individual.

As indicated above, in a preferred method according to the present invention the value measured for IGFBP-7 is at least combined with the value of at least one further marker selected from the group consisting of a natriuretic peptide marker, a cardiac troponin marker, and a marker of inflammation.

In a preferred embodiment the present invention relates to the use of the marker combination IGFBP-7 and NT-proBNP in the assessment of heart failure.

In a preferred embodiment the present invention relates to the use of the marker combination IGFBP-7 and troponin T in the assessment of heart failure.

In a preferred embodiment the present invention relates to the use of the marker combination IGFBP-7 and CRP in the assessment of heart failure.

In a further preferred embodiment the present invention relates to a marker combination comprising the markers IGFBP-7, troponin T, NT-proBNP and CRP.

In yet a further preferred embodiment the present invention relates to a marker panel used in a method for assessing HF in vitro by biochemical markers, comprising measuring in a sample the concentration of IGFBP-7 and of one or more other marker of HF and using the concentrations determined in the assessment of HF.

A marker panel according to the present invention is preferably measured using a protein array technique. An array is a collection of addressable individual markers. Such markers can be spacially addressable, such as arrays contained within microtiter plates or printed on planar surfaces where each marker is present at distinct X and Y coordinates. Alternatively, markers can be addressable based on tags, beads, nanoparticles, or physical properties. The microarrays can be prepared according to the methods known to the ordinarily skilled artisan (see for example, U.S. Pat. No. 5,807,522; Robinson, W. H., et al., Nat. Med. 8 (2002) 295-301; Robinson, W. H., et al., Arthritis Rheum. 46 (2002) 885-893). Array as used herein refers to any immunological assay with multiple addressable markers. In one embodiment the addressable markers are antigens. In another embodiment the addressable elements are autoantibodies. A microarray is a miniaturized form of an array. Antigen as used herein refers to any molecule that can bind specifically to an antibody. The term autoantibody is well-defined in the art.

In a preferred embodiment the present invention relates to a protein array comprising the marker IGFBP-7 and optionally one or more other marker of HF.

In a preferred embodiment the present invention relates to a protein array comprising the markers IGFBP-7 and NT-proBNP.

In a preferred embodiment the present invention relates to a protein array comprising the markers IGFBP-7 and troponin T.

In a preferred embodiment the present invention relates to a protein array comprising the markers IGFBP-7 and CRP.

In a further preferred embodiment the present invention relates to a protein array comprising the markers IGFBP-7, troponin T, NT-proBNP and CRP.

In yet a further preferred embodiment the present invention relates to a kit comprising the reagents required to specifically measure IGFBP-7. Also preferred is a kit comprising the reagents required to specifically measure IGFBP-7 and the reagents required to measure the one or more other marker of heart failure that are used together in an HF marker combination.

The following examples, sequence listing and figures are provided to aid the understanding of the present invention, the true scope of which is set forth in the appended claims. It is understood that modifications can be made in the procedures set forth without departing from the spirit of the invention.

EXAMPLE 1

Mouse Models of Heart Failure 1.1 the R9C Mouse Model

It has been reported that an inherited human dilated cardiomyopathy resulted from the conversion of Arg9 to Cys in the human phospholamban (PLN) gene (PLN-R9C) (Schmitt, J. P., et al., Science 299 (2003) 1410-1413). The onset of dilated cardiomyopathy in affected patients typically commenced during adolescence, followed by progressive deterioration in cardiac function leading to crisis and mortality. A transgenic mouse model of this mutation showed similar cardiac phenotype as the affected patients and presented with dilated cardiomyopathy, decreased cardiac contractility, and premature death (Schmitt et al., 2003, supra).

Figure 1B:
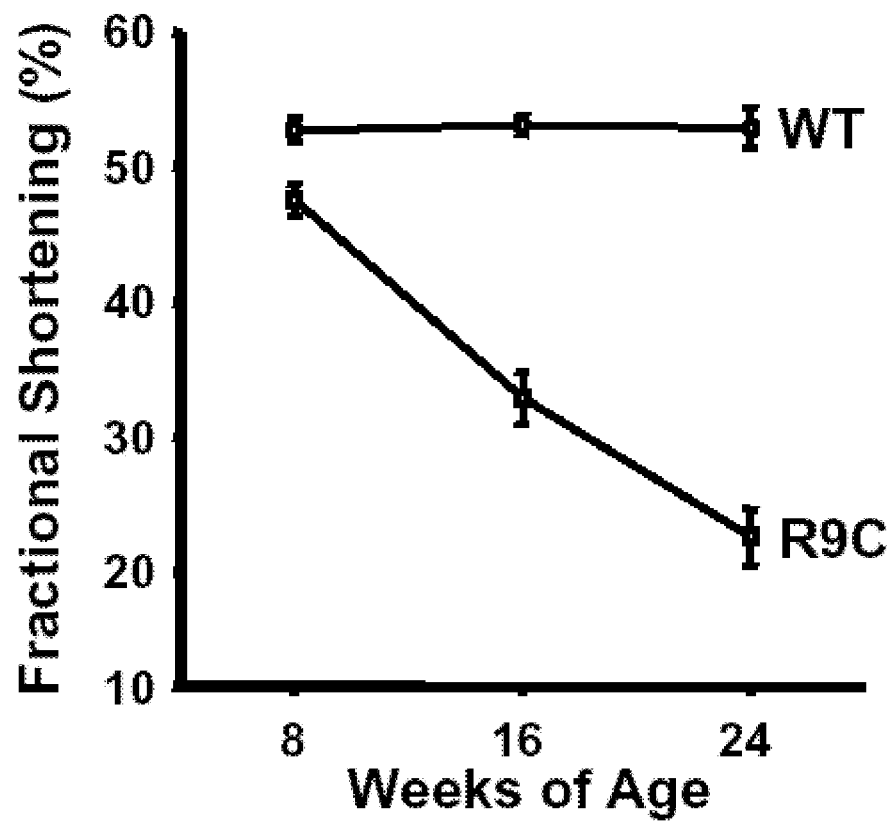
FIG. 1B: (B) Cardiac shortening assessed by echocardiography (=fractional shortening). Significant functional impairment in the R9C transgenic animals begin as early as 8 weeks of age.
Figure 2:
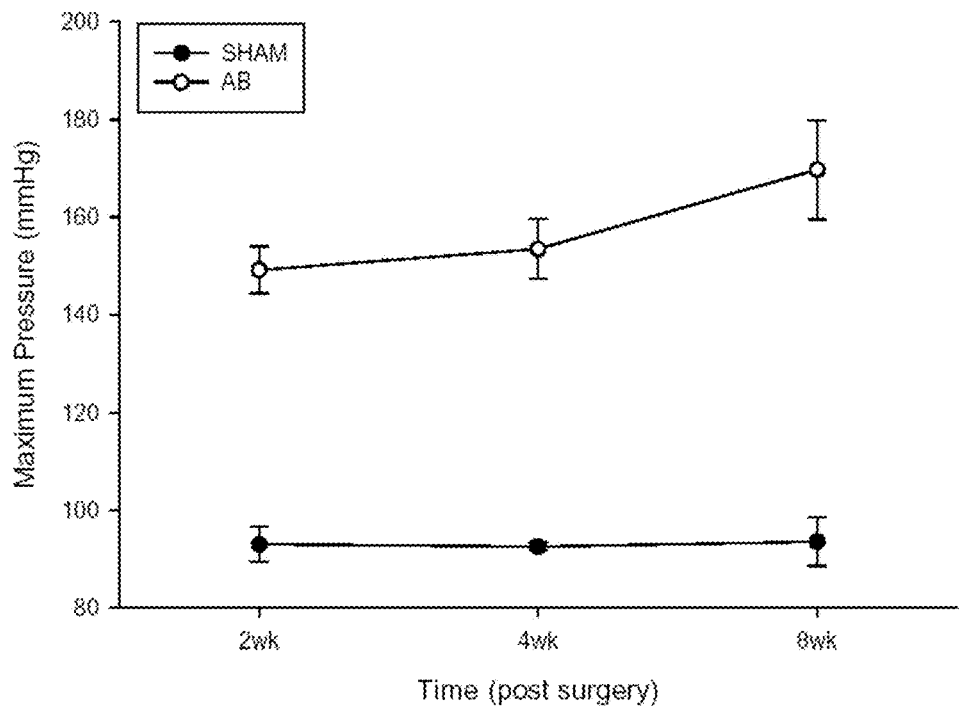
FIG. 2: Echocardiographic and hemodynamic parameters in wildtype and AB mice. (A) Changes in maximum pressure in mmHg at 2, 4, and 8 weeks post surgery. (B) Change in % left ventricular ejection fraction (LVEF) at 2, 4, and 8 weeks after surgery. (Closed circles indicate the data from sham operated mice and open circles indicate the data from mice with aortic binding (AB).
Figure 2:
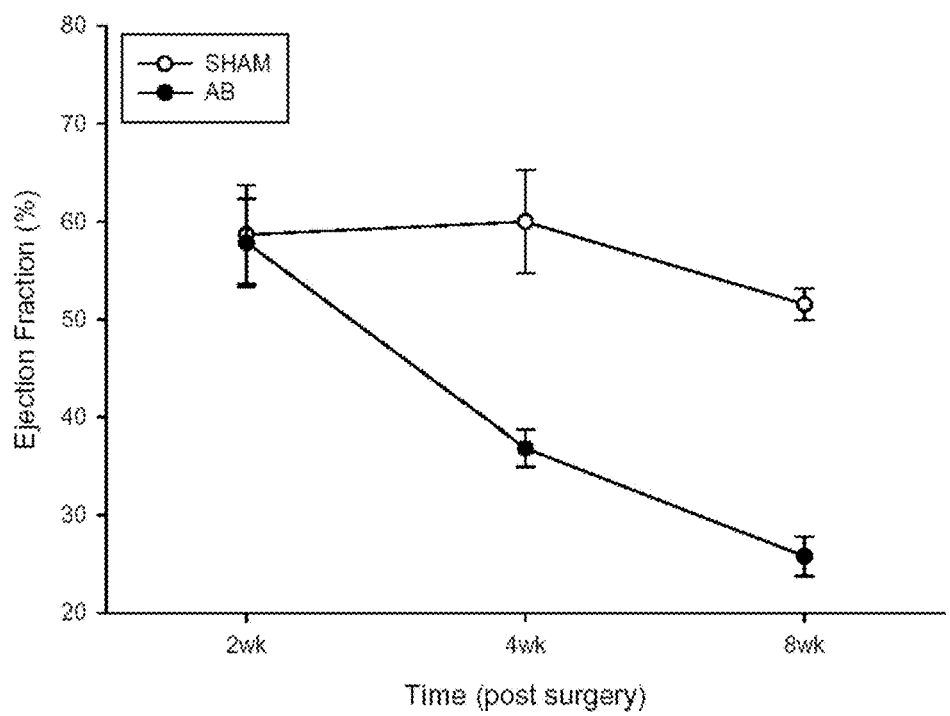

We established a survival curve for the transgenic mice. The PLN-R9C mice had a median survival of only ~20 weeks with fewer than 15% persisting past 24 weeks (FIG. 1 A). The first recorded deaths in the PLN-R9C line are observed at 12 weeks of age, while only one wild-type control mouse died over the 24 week period. Eight weeks is selected as representative time point of 'early' stage disease prior to the first recorded mortality, while 16 weeks is chosen as it is the midpoint between 8 and 24 weeks (classic DCM). A detailed analysis of the pathology of isolated hearts shows evidence of ventricle and atria enlargement even at 8 weeks of age in the PLN-R9C mice. Cross-sections of isolated cardiac muscle (obtained from wild-type and PLN-R9C mice followed by hematoxylin and eosin staining also shows evidence of left ventricular dilatation, or thinning of the ventricular wall, in the transgenic animals beginning at 8 weeks, with continued progression of dilatation with age.

Functional cardiac measurements are performed by echocardiography on the 8, 16 and 24 week old male mice (summarized in Table 1). Echocardiography measurements of the thickness of the anterior and posterior wall show that the R9C mice have significant dilatation at 8 weeks, which continues to deteriorate throughout the lifespan of the mice. Contractility, as assessed by cardiac shortening (FIG. 1 B), is also slightly, but significantly, reduced at 8 weeks, while a more pronounced decrease is clearly evident by 16 weeks. Female mice analyzed show identical findings as the males (data not shown).

TABLE 1

Echocardiographic and hemodynamic parameters in wildtype and R9C mice at 8, 16, and 24 weeks in male mice.

|  | WT | R9C | WT | R9C | WT | R9C |
|---|---|---|---|---|---|---|
| Age | 8 wks | 8 wks | 16 wks | 16 wks | 24 wks | 24 wks |
| Gender | M | M | M | M | M | M |
| HR (bpm) | 560 ± 6 | 567 ± 5 | 569 ± 5 | 552 ± 15 | 565 ± 9 | 502 ± 15* |
| AW (mm) | 0.66 ± 0.01 | 0.60 ± 0.01* | 0.70 ± 0.01 | 0.58 ± 0.01* | 0.71 ± 0.01 | 0.57 ± 0.01* |
| PW (mm) | 0.66 ± 0.01 | 0.61 ± 0.01* | 0.70 ± 0.01 | 0.59 ± 0.01* | 0.71 ± 0.01 | 0.57 ± 0.01* |
| LVEDD (mm) | 3.82 ± 0.05 | 4.01 ± 0.03* | 3.92 ± 0.07 | 5.01 ± 0.06* | 3.99 ± 0.05 | 5.48 ± 0.08* |
| LVESD (mm) | 1.82 ± 0.05 | 2.13 ± 0.04* | 1.84 ± 0.06 | 3.36 ± 0.09* | 1.89 ± 0.03 | 4.23 ± 0.09* |
| FS (%) | 52.7 ± 0.9 | 47.6 ± 1.2* | 53.1 ± 0.7 | 32.9 ± 1.9* | 52.9 ± 1.5 | 22.6 ± 2.1* |
| VCFc (circ/s) | 10.5 ± 0.2 | 9.1 ± 0.2* | 10.5 ± 0.1 | 7.0 ± 0.5* | 10.9 ± 0.3 | 5.1 ± 0.5* |
| PAVc (cm/s) | 102.4 ± 2.4 | 97.8 ± 2.6 | 110.1 ± 3.7 | 85.3 ± 3.2* | 111.3 ± 2.9 | 73.6 ± 3.1* |
| AVA (m/s2) | 65.7 ± 1.3 | 60.6 ± 1.6 | 66 ± 3.2 | 47.9 ± 2.5* | 67.1 ± 3.1 | 40 ± 2.2* |
| Samples (n) | 6 | 9 | 6 | 9 | 5 | 5 |

Values in Table 1 are mean±SEM. Symbols used in Table 1: HR=Heart Rate; AW, PW=Anterior and Posterior Wall Thickness (Left Ventricle); LVEDD, LVESD=Left Ventricular End Diastolic and Systolic Dimension, respectively; FS=Fractional Shortening=(LVEDD−LVESD)/LVEDD× 100%; ETC=Ejection Time corrected for HR; VCFC=Velocity of Circumferential Shortening corrected for HR=FS/ETC; PAVC=Peak Aortic Velocity corrected for HR; E-wave=Early-filling transmitral diastolic wave; LVESP, LVEDP=Left Ventricular End Systolic and Diastolic Pressure; +dP/dtmax=Maximum positive 1st derivative of the left ventricular pressure; −dP/dtmax=Maximum negative 1st derivative of the left ventricular pressure; AVA=aortic velocity acceleration (PAVc/Acceleration Time); *P<0.05 compared with WT.

1.2 the Aortic Banding (AB) Mouse Model

In this mouse model pressure-overload caused by aortic banding (AB) induces cardiac-hypertrophy.

By surgical intervention pressure-overload is performed in C57BL mice. The coarction of the ascending aorta (known as aortic banding) induces cardiac hypertrophy and growth of the myocardial muscle, especially in the left ventricle as a primary response to coarction of the aorta. In the later stages of this mouse model the heart becomes hypertrophic and finally dilated. This model is well characterized and has proven to be highly reproducible with a low mortality rate of 10-15% or less based on experience. After coarction this animal model allows for evaluating the progress of development of left ventricular hypertrophy and heart failure in response to hemodynamic stress.

Briefly C57BL mice are anesthetized with mixed Ketamine (90 mg/kg) and Rompun (10 mg/Kg) and the aorta is ligated using 25-gauge needle. Sham operated mice undergo the same surgical procedure, except that the ligation is not tightened against the needle.

Experimental Time Points

To examine the hypertrophic response, banded animals and sham-operated controls are sacrificed at one, two, four, and eight weeks post intervention. Cardiac function and the development of hypertrophy are assessed by echocardiographic analysis and confirmed post mortem by examining the histology. Table 2 shows an overview over the cardiac function evaluated at the various time points by echocardiography. Details on the echocardiographic parameters given in Table 2 are known to the artisan and can e.g., be found in Asahi, M., et al., Proc. Natl. Acad. Sci. USA 101 (2004) 9199-9204, and Oudit, G. Y., et al., Nat. Med. 9 (2003) 1187-1194.

TABLE 2

| Parameter | 2 wk sham | 2 wk AB | 4 wk sham | 4 wk AB | 8 wk sham | 8 wk AB |
|---|---|---|---|---|---|---|
| Heart rate (bpm) | 271.6 ± 31.2 | 286.32 ± 39.1 | 275.3 ± 25.8 | 276.5 ± 28.1 | 255.5 ± 23.9 | 310.8 ± 18.0 |
| Maximum Volume (uL) | 32.2 ± 2.3 | 36.4 ± 3.4 | 36.9 ± 1.1 | 40.8 ± 1.6 | 38.1 ± 1.5 | 48.9 ± 4.4 |
| Minimum Volume (uL) | 13.7 ± 2.4 | 15.8 ± 3.3 | 14.7 ± 1.9 | 25.7 ± 0.9 | 18.4 ± 0.5 | 36.5 ± 3.7 |
| End-systolic Volume (uL) | 14.7 ± 2.8 | 16.9 ± 3.3 | 15.5 ± 2.1 | 28.0 ± 0.7 | 19.3 ± 0.5 | 40.2 ± 4.3 |
| End-diastolic Volume (uL) | 30.6 ± 2.4 | 34.5 ± 3.2 | 35.2 ± 1.1 | 39.8 ± 1.6 | 36.8 ± 1.4 | 47.2 ± 4.1 |
| Maximum Pressure (mmHg) | 93.1 ± 3.5 | 149.2 ± 4.8 | 92.6 ± 0.8 | 153.5 ± 6.1 | 93.6 ± 5.0 | 169.8 ± 10.2 |
| Minimum Pressure (mmHg) | 4.9 ± 1.3 | 3.2 ± 0.4 | 3.6 ± 0.1 | 7.3 ± 3.6 | 4.1 ± 0.5 | 6.2 ± 1.9 |
| End-systolic Pressure (mmHg) | 87.3 ± 4.3 | 139.4 ± 2.8 | 89.2 ± 1.0 | 149.6 ± 5.0 | 90.5 ± 4.9 | 168.3 ± 9.8 |
| End-diastolic Pressure (mmHg) | 14.0 ± 3.2 | 10.6 ± 2.7 | 13.0 ± 0.7 | 16.8 ± 4.8 | 16.5 ± 1.4 | 16.9 ± 3.1 |
| Stroke Volume (uL) | 18.6 ± 1.0 | 20.6 ± 0.7 | 22.2 ± 2.3 | 15.1 ± 1.2 | 19.7 ± 1.4 | 12.4 ± 1.0 |
| Ejection Fraction (%) | 58.7 ± 5.1 | 57.9 ± 4.5 | 60.0 ± 5.3 | 36.8 ± 1.9 | 51.5 ± 1.6 | 25.8 ± 2.0 |
| Cardiac Output (uL/min) | 5113.5 ± 819.2 | 5879.1 ± 714.0 | 6114.8 ± 897.0 | 4108.6 ± 310.3 | 5066.0 ± 653.3 | 3893.8 ± 466.1 |
| Stroke Work (mmHg*uL) | 1339.6 ± 134.0 | 2196.3 ± 94.6 | 1577.8 ± 134.4 | 1477.8 ± 99.6 | 1451.8 ± 130.4 | 1179.2 ± 104.1 |
| Arterial Elastance (Ea) (mmHg/uL) | 4.8 ± 0.4 | 6.8 ± 0.3 | 4.1 ± 0.4 | 10.1 ± 0.7 | 4.7 ± 0.4 | 14.1 ± 1.7 |
| dPdt max (mmHg/sec) | 5481.6 ± 491.1 | 6785.3 ± 434.2 | 6036.0 ± 352.9 | 5133.2 ± 621.4 | 5755.8 ± 652.9 | 6454.4 ± 712.0 |
| dPdt min (mmHg/sec) | −5049.6 ± 426.9 | −7427.5 ± 685.3 | −4743.3 ± 287.7 | −5484.75 ± 412.2 | −4564.5 ± 525.8 | −7625 ± 586.5 |

TABLE 2-continued

| Parameter | 2 wk sham | 2 wk AB | 4 wk sham | 4 wk AB | 8 wk sham | 8 wk AB |
|---|---|---|---|---|---|---|
| dVdt max (uL/sec) | 883.0 ± 61.2 | 758.0 ± 29.8 | 856.5 ± 27.4 | 1152.8 ± 206.3 | 1188.0 ± 114.1 | 1041.2 ± 109.6 |
| dVdt min (uL/sec) | −679.6 ± 71.4 | −696.3 ± 30.6 | −703.5 ± 52.2 | −921.0 ± 158.0 | −1000.5 ± 76.8 | −938.4 ± 126.2 |
| P@dVdt max (mmHg) | 9.0 ± 2.5 | 7.4 ± 2.6 | 4.6 ± 0.4 | 10.3 ± 3.4 | 6.2 ± 1.0 | 13.3 ± 4.5 |
| P@dPdt max (mmHg) | 44.1 ± 2.1 | 46.3 ± 3.5 | 49.0 ± 2.6 | 47.1 ± 2.8 | 49.6 ± 5.6 | 52.8 ± 3.6 |
| V@dPdt max (uL) | 31.2 ± 2.4 | 35.5 ± 3.5 | 35.0 ± 1.1 | 39.7 ± 1.6 | 37.0 ± 1.5 | 47.3 ± 4.4 |
| V@dPdt min (uL) | 14.7 ± 2.6 | 17.1 ± 3.2 | 15.6 ± 1.9 | 27.0 ± 0.7 | 19.2 ± 0.4 | 39.0 ± 4.3 |
| Tau_w (msec) | 11.4 ± 1.2 | 8.6 ± 0.7 | 10.7 ± 0.9 | 11.2 ± 1.3 | 11.3 ± 0.5 | 8.8 ± 0.4 |
| Tau_g (msec) | 15.8 ± 1.5 | 12.1 ± 1.2 | 17.5 ± 0.7 | 17.4 ± 1.0 | 17.5 ± 1.0 | 15.6 ± 1.0 |
| Maximal Power (mWatts) | 6.4 ± 0.6 | 9.5 ± 0.4 | 6.8 ± 0.5 | 8.8 ± 0.5 | 7.3 ± 0.7 | 9.0 ± 0.5 |
| Preload adjusted maximal power (mWatts/← N5L^2) | 74.8 ± 16.5 | 85.0 ± 12.9 | 55.5 ± 2.4 | 57.3 ± 7.4 | 53.6 ± 3.0 | 46.1 ± 11.5 |

In addition to functional parameters histology by Hematoxylin/Eosin (HE) staining is performed on cardiac tissue from AB mice and control mice at 2, 4, and 8 weeks. Histology confirms the expected necrotic and remodeling processes for the AB mice, whereas heart tissue in sham operated mice does not show any significant changes. At two weeks after surgery the ventricle of a ligated mouse shows significant left ventricular hypertrophy which after four weeks has further progressed and at eight weeks post surgery closely resembles end stage dilated cardiomyopathy.

EXAMPLE 2

Sample Preparation and Mass Spectroscopy

Heart Homogenization and Organelle Isolation

Hearts are isolated, atria removed, the ventricles carefully minced with a razor blade and rinsed extensively with ice-cold PBS (phosphate buffered saline) to remove excess blood. Tissue is homogenized for 30 s using a loose fitting hand-held glass homogenizer in 10 ml lysis buffer (250 mM sucrose, 50 mM Tris-HCl pH 7.6, 1 mM MgCl2, 1 mM DDT (dithiothreitol), and 1 mM PMSF (phenylmethylsulphonyl fluoride). All subsequent steps are performed at 4° C. The lysate is centrifuged in a benchtop centrifuge at 800×g for 15 min; the supernatant serves as a source for cytosol, mitochondria, and microsomal fractions. The pellet containing nuclei is diluted in 8 ml of lysis buffer and layered onto 4 ml of 0.9 M sucrose buffer (0.9 M sucrose, 50 mM Tris-HCl pH 7.6, 1 mM MgCl2, 1 mM DDT, and 1 mM PMSF) and centrifuged at 1000×g for 20 min at 4° C. The resulting pellet is resuspended in 8 ml of a 2 M sucrose buffer (2 M sucrose, 50 mM Tris-HCl pH 7.4, 5 mM MgCl2, 1 mM DTT, and 1 mM PMSF), layered onto 4 ml of 2 M sucrose buffer and pelleted by ultracentrifugation at 150,000×g for 1 h (Beckman SW40.1 rotor). The nuclei are recovered as a pellet. The mitochondria are isolated from the supernatant by re-centrifugation at 7500×g for 20 min at 4° C.; the resulting pellet is washed twice in lysis buffer. Microsomes are pelleted by ultracentrifugation of the post-mitochondrial cytoplasm at 100,000×g for 1 h in a Beckman SW41 rotor. The supernatant served as the cytosolic fraction (=cyto).

Organelle Extraction

Soluble mitochondrial proteins are extracted by incubating the mitochondria in hypotonic lysis buffer (10 mM HEPES, pH 7.9, 1 mM DTT, 1 mM PMSF), for 30 min on ice. The suspension is sonicated briefly and debris removed by centrifugation at 13,000×g for 30 min. The supernatant serves as the "mito 1" fraction. The resulting insoluble pellet is resuspended in membrane detergent extraction buffer (20 mM Tris-HCl, pH 7.8, 0.4 M NaCl, 15% glycerol, 1 mM DTT, 1 mM PMSF, 1.5% Triton-X-100) and shaken gently for 30 min followed by centrifugation at 13,000×g for 30 min; the supernatant served as "mito 2" fraction.

Membrane-associated proteins are extracted by resuspending the microsomes in membrane detergent extraction buffer. The suspension is incubated with gentle shaking for 1 h and insoluble debris removed by centrifugation at 13,000×g for 30 min. The supernatant serves as the "micro" fraction.

Digestion of Organelle Extracts and MudPIT Analysis

An aliquot of about 100 µg total protein (as determined by Bradford assay) from each fraction is precipitated overnight with 5 vol of ice-cold acetone at about 20° C., followed by centrifugation at 13,000×g for 15 min. The protein pellet is solubilized in a small volume of 8 M urea, 50 mM Tris-HCl, pH 8.5, 1 mM DTT, for 1 h at 37° C., followed by carboxyamidomethylation with 5 mM iodoacetamide for 1 h at 37° C. in the dark. The samples are then diluted to 4 M urea with an equal vol of 100 mM ammonium bicarbonate, pH 8.5, and digested with a 1:150-fold ratio of endoproteinase Lys-C(Roche Diagnostics, Laval, Quebec, Canada) at 37° C. overnight. The next day, the samples are diluted to 2 M urea with an equal vol of 50 mM ammonium bicarbonate pH 8.5, supplemented with CaCl2 to a final concentration of 1 mM, and incubated overnight with Poroszyme trypsin beads (Applied Biosystems, Streetsville, Ontario, Canada) at 30° C. with rotation. The resulting peptide mixtures are solid phase-extracted with SPEC-Plus PT C18 cartridges (Ansys Diagnostics, Lake Forest, Calif.) according to the instructions of the manufacturer and stored at −80° C. until further use. A fully-automated 20 h long 12-step multi-cycle MudPIT procedure is set up as described (Kislinger, T., et al., Mol. Cell Proteom. 2 (2003) 96-106). Briefly, an HPLC quaternary pump is interfaced with an LCQ DECA XP ion trap mass spectrometer (Thermo Finnigan, San Jose, Calif.). A 100-µm i.d. fused silica capillary microcolumn (Polymicro Technologies, Phoenix, Ariz.) is pulled to a fine tip using a P-2000 laser puller (Sutter Instruments, Novato, Calif.) and packed with 8 cm of 5 µm Zorbax Eclipse XDB-C18 resin (Agilent Technologies, Mississauga, Ontario, Canada), followed by 6 cm of 5 µm Partisphere strong cation exchange resin (Whatman, Clifton, N.J.). Individual samples are loaded manually onto separate columns using a pressure vessel. Chromatography solvent conditions are exactly as described in Kislinger, T., et al., Mol. Cell Proteom. 2 (2003) 96-106.

Protein Identification and Validation

The SEQUEST database search algorithm is used to match peptide tandem mass spectra to peptide sequences in a locally-maintained minimally redundant FASTA formatted database populated with mouse and human protein sequences obtained from the Swiss-Prot/TrEMBL and IPI databases. To statistically assess the empirical False-Discovery Rate to control for, and hence, minimize false positive identifications, all of the spectra are searched against protein sequences in both the normal (Forward) and inverted (Reverse) amino acid orientations (Kislinger, T., et al., Mol. Cell Proteom. 2 (2003) 96-106). The STATQUEST filtering algorithm is then applied to all putative search results to obtain a measure of the statistical reliability (confidence score) for each candidate identification (cutoff p-value ≤0.15, corresponding to an 85% or greater likelihood of being a correct match). High-confidence matches are parsed into an in-house SQL-type database using a Perl-based script. The database is designed to accommodate database search results and spectral information (scan headers) for multiple peptides matching to a given protein, together with information regarding the sample name, experiment number, MudPIT step, organelle source, amino acid sequence, molecular mass, isoelectric point, charge, and confidence level. Only those proteins with a predicted confidence p value of 95% or more, and for which at least two spectra are collectively detected, are retained for further analysis.

EXAMPLE 3

Statistical Evaluation of the Data Obtained in the Model Systems 3.1 Statistical Methods Used to Generate p-Values of Differential Expression for the R9C Mouse Model The raw data obtained with the methods as described in Example 2 consists of 6190 proteins each with spectral counts, the sum of all spectra associated with the protein, for each of the 137 different experimental runs. The raw data, 6190 subset of proteins, is subjected to global normalization which first separates the data within each run into an equal number of groups, set at 100 for our analysis, based on their spectral counts. LOESS (Cleveland, W. S. and Devlin, S. J., Journal of the American Statistical Association 83 (1988) 596-610) is then performed on each group (1-100) adjusting for differences in spectral counts across a set of genes with similar spectral counts.

Based on our raw data we constructed two linear models, the first model uses control/disease, time (8W, 16W, end) and location (cyto, micro, mitoI, mitoII) as factors and is described using:

$$\text{run count}=\beta 0+\beta 1\text{time}+\beta 2\text{time}^2+\beta 3\text{location}+\beta 4\text{control} \quad (1)$$

The second model uses only time (8W, 16W, end) and location (cyto, micro, mitoI, mitoII) as factors and is described using:

$$\text{run count}=\beta 0+\beta 1\text{time}+\beta 2\text{time}^2+\beta 3\text{location} \quad (2)$$

where β0 is the intercept term and β1, β2, β3, and β4 are the slope estimates for the variables time, time squared, location, and control/disease.

The two models are compared using Anova, with the null hypothesis being that there is no difference between the two models. A low p-value then indicates that there is not enough proof to say the two models are the same. The extra information indicates the state (i.e., control/disease) appears to be a significant component of the model. In order to extract proteins that have a significant change in relative protein abundance between our control and disease models our list of 6190 proteins is ranked based on their computed p-values. This generates a set of 593 proteins with p-values <0.05.

In order to account for multiple hypothesis testing from the above model the p-values are then corrected using false discovery rate (FDR) correction, specifically Benjamini-Hochberg FDR correction (Benjamini, Y., and Hochberg, Y., Journal of the Royal Statistical Society B. 57 (1995) 289-300). This generates a set of 40 proteins with corrected p-values <0.05 for the R9C mouse model.

3.2 Statistical Methods Used to Generate p-Values of Differential Expression for the Aortic Banding Mouse Model From 68 experimental runs in the aortic banding mouse model 3152 proteins with spectral counts are identified. The same data analysis is applied to the datasets for the aortic banding mouse model as described above for the R9C mouse model.

EXAMPLE 4

Detection of the Marker IGFBP-7 by Western Blot Assay

Crude tissue lysates are obtained from R9C mouse heart tissue samples. In brief, heart tissue is minced, ground up in a dounce homogenizer and subjected to a centrifuge spin of 8,000 g for 30 min to remove nuclei and cell debris. The supernatant is used for Western Blotting.

Figure 3:
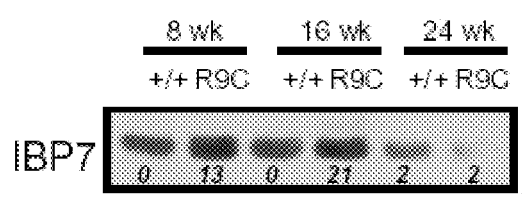
FIG. 3: Western Blotting data as obtained with cardiac tissue from R9C and control mice, respectively. A strong overexpression of IGFBP-7 is observed in tissue samples derived from experimental (R9C) animals suffering from heart failure versus tissue samples derived from healthy mice (=+/+). Numbers underneath the stained bands indicate relative expression levels determined by the numbers of mass spectra recorded.

SDS-PAGE and Western-Blotting are carried out using reagents and equipment of Invitrogen, Karlsruhe, Germany. For each tissue sample tested, 10 μg of the cytosolic fraction are diluted in reducing NuPAGE (Invitrogen) SDS sample buffer and heated for 10 min at 95° C. Samples are run on 4-12% NuPAGE gels (Tris-Glycine) in the MES running buffer system. The gel-separated protein mixture is blotted onto nitrocellulose membranes using the Invitrogen XCell II Blot Module (Invitrogen) and the NuPAGE transfer buffer system. The membranes are washed 3 times in PBS/0.05% TWEEN-20® polysorbate 20 (ICI Americas Inc.) and blocked with Roti-Block blocking buffer (A151.1; Carl Roth GmbH, Karlsruhe, Germany) for 2 h. The primary antibody, rabbit polyclonal to calreticulin (PA1-903, Affinity Bioreagents (ABR), Golden, Colo.) is diluted 1:500 in Roti-Block blocking buffer and incubated with the membrane for 1 h. The membranes are washed 6 times in PBS/0.05% TWEEN-20® polysorbate 20. The specifically bound primary IGFBP-7 antibody is labeled with a POD-conjugated polyclonal anti-rat IgG antibody, diluted to 10 mU/ml in 0.5× Roti-Block blocking buffer. After incubation for 1 h, the membranes are washed 6 times in PBS/0.05% TWEEN-20® polysorbate 20. For detection of the bound POD-conjugated anti-rabbit antibody, the membrane is incubated with the Lumi-LightPLUS Western Blotting Substrate (Order-No. 2015196, Roche Diagnostics GmbH, Mannheim, Germany) and exposed to an autoradiographic film. Results of a typical experiment are shown in FIG. 3. A strong overexpression of IGFBP-7 is observed in tissue samples derived R9C experimental animals suffering from heart failure versus tissue samples derived from a healthy mouse at matching time points.

EXAMPLE 5

5.1. ELISA for the Measurement of IGFBP-7 in Human Serum and Plasma Samples

For detection of IGFBP-7 in human serum or plasma, a sandwich ELISA is developed. For capture and detection of the antigen, aliquots of an anti-IGFBP-7 polyclonal antibody from R&D Systems (Catalogue number: AF 1334) is conjugated with biotin and digoxygenin, respectively.

Streptavidin-coated 96-well microtiter plates are incubated with 100 μl biotinylated anti-IGFBP-7 polyclonal antibody for 60 min at 1 μg/ml in 1×PBS solution. After incubation, plates are washed three times with 1×PBS+ 0.02% TWEEN-20® polysorbate 20, blocked with PBS+1% BSA (bovine serum albumen) and then washed again three times with 1×PBS+0.02% TWEEN-20® polysorbate 20. Wells are then incubated for 1.5 h with either a serial dilution of the recombinant IGFBP-7 as standard antigen or with diluted serum or plasma samples (1:50) from patients or control individuals, respectively. After binding of IGFBP-7, plates are washed three times with 1×PBS+0.02% TWEEN-20® polysorbate 20. For specific detection of bound IGFBP-7, wells are incubated with 100 μl of digoxigenylated anti-IGFBP-7 polyclonal antibody for 60 min at 1 μg/ml in 1×PBS+1% BSA. Thereafter, plates are washed three times to remove unbound antibody. In a next step, wells are incubated with 75 mU/ml anti-digoxigenin-POD conjugates (Roche Diagnostics GmbH, Mannheim, Germany, Catalog No. 1633716) for 60 min in 1×PBS+1% BSA. Plates are subsequently washed six times with the same buffer. For detection of antigen-antibody complexes, wells are incubated with 100 μl ABTS solution (Roche Diagnostics GmbH, Mannheim, Germany, Catalog No. 11685767) and the optical density (OD) is measured after 15 min at 405 and 492 nm with an ELISA reader.

5.2. Test of IGFBP7 ELISA in Samples Derived from Patients with Heart Failure and Apparently Healthy Donors, Respectively For the establishment and optimization of the IGFBP-7 ELISA 10 serum samples obtained from different patients with heart failure (HF samples) and 10 sera of normal healthy donors (NHS) are tested. After performing the assay procedure as described in 5.1 the following results (see Table 3) are obtained with these samples:

TABLE 3

IGFBP7 ELISA results (assay development samples)

|     |      | Delta OD | Conc [ng/mL * 50] |       |        | Delta OD | ng/mL Conc | Conc calculated |
| --- | ---- | -------- | ----------------- | ----- | ------ | -------- | ---------- | --------------- |
| HF  | 5078 | 0.351    | 0.108             | 5.4   | Median | 0.421    | 0.15       | 7.33            |
|     | 5084 | 0.582    | 0.231             | 11.55 | Min    | 0.229    | 0.03       | 1.55            |
|     | 5085 | 0.435    | 0.154             | 7.7   | Max    | 0.957    | 0.42       | 21.00           |
|     | 5100 | 0.304    | 0.080             | 4     | MW     | 0.4645   | 0.17       | 8.30            |
|     | 5101 | 0.537    | 0.208             | 10.4  |        |          |            |                 |
|     | 5104 | 0.556    | 0.218             | 10.9  |        |          |            |                 |
|     | 5107 | 0.407    | 0.139             | 6.95  |        |          |            |                 |
|     | 5112 | 0.287    | 0.070             | 3.5   |        |          |            |                 |
|     | 5113 | 0.957    | 0.420             | 21    |        |          |            |                 |
|     | 5144 | 0.229    | 0.031             | 1.55  |        |          |            |                 |
| NHS | 34   | 0.372    | 0.120             | 6     | Median | 0.256    | 0.05       | 2.48            |
|     | 35   | 0.254    | 0.048             | 2.4   | Min    | 0.204    | 0.01       | 0.55            |
|     | 36   | 0.254    | 0.048             | 2.4   | Max    | 0.377    | 0.12       | 6.10            |
|     | 37   | 0.288    | 0.070             | 3.5   | MW     | 0.2718   | 0.06       | 2.90            |
|     | 38   | 0.258    | 0.051             | 2.55  |        |          |            |                 |
|     | 39   | 0.234    | 0.035             | 1.75  |        |          |            |                 |
|     | 40   | 0.263    | 0.055             | 2.75  |        |          |            |                 |
|     | 41   | 0.214    | 0.019             | 0.95  |        |          |            |                 |
|     | 42   | 0.204    | 0.011             | 0.55  |        |          |            |                 |
|     | 43   | 0.377    | 0.122             | 6.1   |        |          |            |                 |

Figure 4:
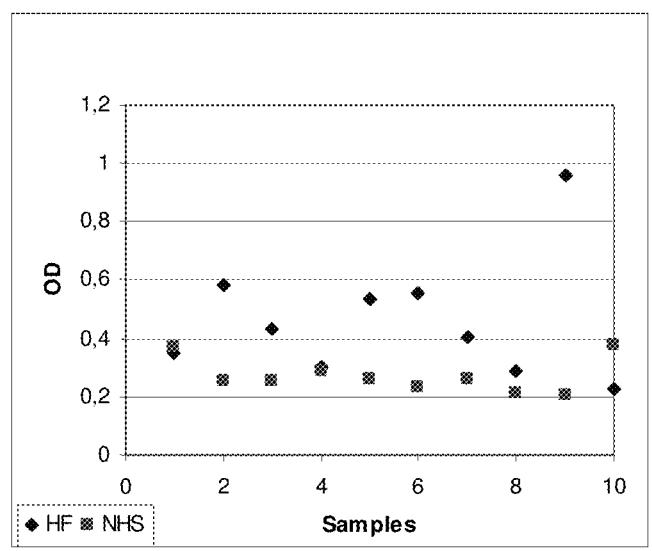
FIG. 4: IGFBP-7 measured in 10 HF and control samples, respectively. Optical densities (ODs) in the IGFBP-7 assay are given for samples derived from patients with heart failure are labeled (HF=rhombi), and for healthy controls (normal human serum=NHS=squares), respectively.

As obvious from FIG. 4 the IGFBP-7 levels are in average much higher in the sera obtained from patients with HF as compared to the levels found in the samples obtained from control individuals.

5.3. IGFBP7 ELISA with Sera of Patients have HF and Obtained Out of the Clinical Routine and Apparently Healthy Donors, Respectively In order to further evaluate the utility of the IGFBP-7 assays under routine clinical conditions a panel of sera from HF patients (n=45) and of 35 sera from apparently healthy control patients is investigated. As mentioned before, sera are diluted 1:50 in 1×PBS+1% BSA. Table 4 shows the result for these extended panels:

TABLE 4

IGFBP7 ELISA results (extended panel with HF samples from clinical routine)

| Heart Failure Sera (HF-Panel) | | | | Normal Controls | | | |
| --- | --- | --- | --- | --- | --- | --- | --- |
| n = 45 | | Conc [ng/mL] | | n = 35 | | Conc [ng/mL] | |
| Sample No. | Delta OD | measured | calculated (*50) | Sample No. | Delta OD | measured | calculated (*50) |
| 4143 | 0.236 | 0.07 | 3.40 | 31 | 0.172 | 0.02 | 0.95 |
| 4144 | 0.236 | 0.07 | 3.35 | 32 | 0.334 | 0.13 | 6.65 |

TABLE 4-continued

IGFBP7 ELISA results (extended panel with HF samples from clinical routine)

| Heart Failure Sera (HF-Panel) | | | | Normal Controls | | | |
|---|---|---|---|---|---|---|---|
| n = 45 | | Conc [ng/mL] | | n = 35 | | Conc [ng/mL] | |
| Sample No. | Delta OD | measured | calculated (*50) | Sample No. | Delta OD | measured | calculated (*50) |
| 4145 | 0.223 | 0.06 | 2.90 | 33 | 0.21 | 0.05 | 2.45 |
| 4146 | 0.244 | 0.07 | 3.65 | 44 | 0.257 | 0.08 | 4.10 |
| 4150 | 0.35 | 0.14 | 7.20 | 45 | 0.489 | 0.23 | 11.55 |
| 4151 | 0.347 | 0.14 | 7.10 | 46 | 0.224 | 0.06 | 2.95 |
| 4152 | 0.437 | 0.20 | 9.95 | 47 | 0.226 | 0.06 | 3.00 |
| 4153 | 0.235 | 0.07 | 3.35 | 48 | 0.183 | 0.03 | 1.40 |
| 4154 | 0.253 | 0.08 | 4.00 | 49 | 0.171 | 0.02 | 0.90 |
| 4155 | 0.271 | 0.09 | 4.60 | 50 | 0.29 | 0.11 | 5.25 |
| 4157 | 0.615 | 0.31 | 15.45 | 51 | 0.314 | 0.12 | 6.00 |
| 4158 | 0.419 | 0.19 | 9.40 | 52 | 0.301 | 0.11 | 5.60 |
| 4159 | 0.36 | 0.15 | 7.55 | 53 | 0.232 | 0.07 | 3.25 |
| 4161 | 0.232 | 0.07 | 3.25 | 54 | 0.235 | 0.07 | 3.35 |
| 4162 | 0.345 | 0.14 | 7.05 | 55 | 0.222 | 0.06 | 2.90 |
| 4163 | 0.27 | 0.09 | 4.55 | 56 | 0.343 | 0.14 | 7.00 |
| 4164 | 0.402 | 0.18 | 8.85 | 57 | 0.214 | 0.05 | 2.60 |
| 4170 | 0.833 | 0.44 | 22.20 | 58 | 0.27 | 0.08 | 3.95 |
| 4171 | 0.625 | 0.32 | 15.75 | 59 | 0.389 | 0.15 | 7.65 |
| 4172 | 0.56 | 0.28 | 13.75 | 60 | 0.214 | 0.04 | 2.05 |
| 4173 | 0.396 | 0.17 | 8.70 | 61 | 0.252 | 0.07 | 3.35 |
| 4174 | 0.52 | 0.25 | 12.55 | 62 | 0.183 | 0.02 | 0.90 |
| 4175 | 0.251 | 0.08 | 3.90 | 63 | 0.204 | 0.03 | 1.70 |
| 4176 | 0.352 | 0.13 | 6.55 | 64 | 0.208 | 0.04 | 1.85 |
| 4178 | 0.224 | 0.05 | 2.40 | 65 | 0.228 | 0.05 | 2.55 |
| 4181 | 0.491 | 0.21 | 10.70 | 66 | 0.337 | 0.12 | 6.05 |
| 4182 | 0.352 | 0.13 | 6.55 | 67 | 0.239 | 0.06 | 2.95 |
| 4187 | 0.766 | 0.38 | 18.80 | 68 | 0.235 | 0.06 | 2.80 |
| 4189 | 0.578 | 0.27 | 13.25 | 69 | 0.163 | 0.01 | 0.55 |
| 4190 | 0.28 | 0.09 | 4.30 | 70 | 0.224 | 0.05 | 2.40 |
| 4191 | 0.297 | 0.10 | 4.85 | 71 | 0.214 | 0.04 | 2.05 |
| 4192 | 0.317 | 0.11 | 5.45 | 72 | 0.265 | 0.08 | 3.80 |
| 4193 | 0.476 | 0.21 | 10.25 | 73 | 0.231 | 0.05 | 2.65 |
| 4194 | 0.428 | 0.18 | 8.85 | 74 | 0.25 | 0.07 | 3.30 |
| 4196 | 0.236 | 0.06 | 2.80 | 75 | 0.281 | 0.09 | 4.35 |
| 4198 | 0.333 | 0.12 | 5.95 | Min | 0.163 | 0.01 | 0.55 |
| 4199 | 0.342 | 0.13 | 6.25 | Max | 0.489 | 0.23 | 11.55 |
| 4200 | 0.298 | 0.10 | 4.90 | MW | 0.252 | 0.07 | 3.57 |
| 4202 | 0.556 | 0.25 | 12.60 | Median | 0.232 | 0.06 | 2.95 |
| 4203 | 0.895 | 0.45 | 22.65 | | | | |
| 4204 | 0.52 | 0.23 | 11.60 | | | | |
| 4205 | 0.463 | 0.20 | 9.85 | | | | |
| 4206 | 0.333 | 0.12 | 5.95 | | | | |
| 4212 | 0.267 | 0.08 | 3.85 | | | | |
| 4213 | 0.754 | 0.37 | 18.45 | | | | |
| Min | 0.223 | 0.05 | 2.40 | | | | |
| Max | 0.895 | 0.45 | 22.65 | | | | |
| MW | 0.405 | 0.17 | 8.43 | | | | |
| Median | 0.350 | 0.14 | 7.05 | | | | |

Figure 5:
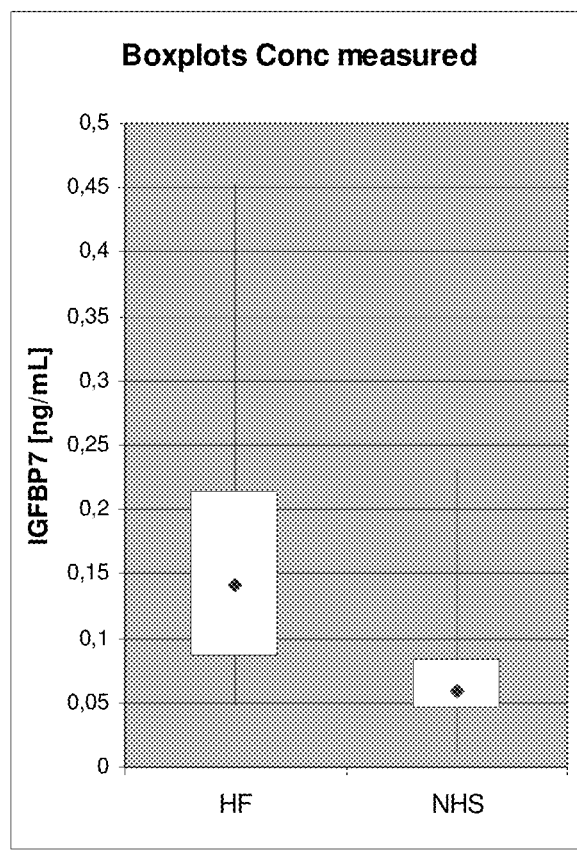
FIG. 5: IGFB-7 values as detected in HF samples from clinical routine and in an extended control panel, respectively. Calculated concentrations are given for IGFBP-7 as measured in samples derived from patients with heart failure are labeled (HF) and in samples from healthy controls (normal human serum=NHS), respectively. The box-and-whisker-blots show the lower and upper quartiles (boxes) as well as the highest and lowest values (whiskers).

The data summarized in Table 4 have been used to calculate the box-blots shown in FIG. 5. FIG. 5 demonstartes that there is quite a difference in the average IGFBP-7 values as measured in sera derived from patients with heart failure as compared to IGFBP-7 values as measured in sera derived from apparently healthy control individuals.

EXAMPLE 6

Marker Combinations Comprising the Marker IGFBP-7 in the Assessment of Heart Failure Example 6.1 The Marker Combination NT-proBNP and IGFBP-7

The marker combination NT-proBNP and IGFBP-7 is evaluated for the differentiation of patients in stage B and stages C plus D, respectively. Diagnostic accuracy is assessed by analyzing individual liquid samples obtained from well-characterized groups of individuals, i.e., 50 individuals in stage B according to the ACA/ACC criteria for classification of HF and 50 patients suffering from HF and having stage C according to the ACA/ACC criteria for classification of HF. NT-proBNP as measured by a commercially available assay (Roche Diagnostics, NT-proBNP-assay (Cat. No. 03 121 640 160 for ELECSYS Systems immunoassay analyzer) and IGFBP-7 measured as described above are quantified in a serum sample obtained from each of these individuals. ROC-analysis is performed according to Zweig, M. H., and Campbell, G., supra. Discriminatory power for differentiating patients in stage C from individuals in stage B for the combination of IGFBP-7 with the established marker NT-proBNP is calculated by regularized discriminant analysis (Friedman, J. H., Regularized Discriminant Analysis, Journal of the American Statistical Association 84 (1989) 165-175).

Example 6.2 The Marker Combination Troponin T and IGFBP-7

The marker combination troponin T and IGFBP-7 is evaluated for the differentiation of patients suffering from an acute cardiac event from patients suffering from chronic heart disease, respectively. Diagnostic accuracy is assessed by analyzing individual liquid samples obtained from well-characterized groups of individuals, i.e., 50 individuals diagnosed as having an acute cardiac event and 50 individuals diagnosed as having chronic cardiac disease. Troponin T as measured by a commercially available assay (Roche Diagnostics, troponin T-assay (Cat. No. 201 76 44 for ELECSYS Systems immunoassay analyzer) and IGFBP-7 measured as described above are quantified in a serum sample obtained from each of these individuals. ROC-analysis is performed according to Zweig, M. H., and Campbell, G., supra. Discriminatory power for differentiating patients in stage C from individuals in stage B for the combination of IGFBP-7 with the established marker NT-proBNP is calculated by regularized discriminant analysis (Friedman, J. H., J. of the American Statistical Association 84 (1989) 165-175).

Example 6.3 The Marker Combination IGFBP-7 and CRP

The marker combination C-reactive protein and IGFBP-7 is evaluated for the differentiation of patients diagnosed as having a cardiomyopathy versus controls not suffering from any confounding heart disease, respectively. Diagnostic accuracy is assessed by analyzing individual liquid samples obtained from well-characterized groups of 50 individuals with cardiomyopathy and of 50 healthy control individuals. CRP as measured by a commercially available assay (Roche Diagnostics, CRP-assay (Tina-quant C-reactive protein (latex) high sensitive assay—Roche Cat. No. 11972855 216) and IGFBP-7 measured as described above are quantified in a serum sample obtained from each of these individuals. ROC-analysis is performed according to Zweig, M. H., and Campbell, G., supra. Discriminatory power for differentiating patients in stage C from individuals in stage B for the combination of IGFBP-7 with the established marker NT-proBNP is calculated by regularized discriminant analysis (Friedman, J. H., J. of the American Statistical Association 84 (1989) 165-175).

While the foregoing invention has been described in some detail for purposes of clarity and understanding, it will be appreciated by one skilled in the art, from a reading of the disclosure that various changes in form and detail can be made without departing from the true scope of the invention in the appended claims.

---

What is claimed is:

1. A method for assessing heart failure in an individual comprising the steps of:
    measuring in a serum, plasma or whole blood sample obtained from the individual a concentration of insulin like growth factor binding protein 7 (IGFBP-7) using an enzyme-linked immunosorbent assay (ELISA) comprising a polyclonal antibody having specific binding affinity for IGFBP-7, said ELISA having an IGFBP-7 detection limit of at least 0.01 ng/mL;
    determining a concentration of IGFBP-7 in a control serum, plasma or whole blood sample from a healthy individual;
    optionally measuring in the sample a concentration of an additional marker of heart failure;
    optionally determining a concentration of the additional marker of heart failure in the control sample;
    assessing heart failure by comparing the concentration(s) determined in the sample the individual to the concentration(s) determined in the control sample;
    determining that the concentration of IGFBP-7 in the sample from the individual is greater than the control concentration; and
    administering one or more of: an angiotensin-converting enzyme (ACE) inhibitor, a beta-blocker, an angiotensin II (AT II) inhibitor, an aldosterone antagonist, and an endothelin-1 blocking agent to the individual assessed as having a greater concentration of IGFBP-7 compared to the control concentration.

2. The method of claim 1 wherein the additional marker is selected from the group consisting of a natriuretic peptide marker, a cardiac troponin marker, and a marker of inflammation.

3. The method of claim 2 wherein the natriuretic peptide marker is NT-proBNP.

4. The method of claim 2 wherein the cardiac troponin marker is troponin T.

5. The method of claim 1 wherein the individual is at risk for heart failure.

6. A kit for performing the method according to claim 1, the kit comprising ELISA reagents required to specifically measure IGFBP-7 protein with a detection limit of 0.01 ng/mL, and reagents for measuring the optional additional marker of heart failure.

7. A method for diagnosing and treating heart failure in an individual comprising the steps of:
    contacting a portion of a sample obtained from the individual with a polyclonal antibody having specific binding affinity for insulin like growth factor binding protein 7 (IGFBP-7), thereby forming a complex between the antibody and IGFBP-7, the antibody having a detectable label, the sample being one of serum, plasma or whole blood;
    separating the complex formed in said step of contacting from antibody not comprising the complex;
    quantifying a signal from the detectable label of the antibody comprising the complex formed in said step of contacting, the signal being proportional to an amount of IGFBP-7 in the sample from the individual, whereby a concentration of IGFBP-7 in the sample is calculated with a detection limit of at least 0.01 ng/mL;
    comparing the concentration of IGFBP-7 calculated in said step of quantifying to a concentration of IGFBP-7 in a control sample comprising one or more healthy individuals;
    providing a diagnosis of heart failure in the individual when the concentration of IGFBP-7 calculated in said step of quantifying in the sample from the individual is greater than the concentration of IGFBP-7 in the control sample; and when diagnosed with heart failure,
    administering one or more of: an angiotensin-converting enzyme (ACE) inhibitor, a beta-blocker, an angiotensin II (AT II) inhibitor, an aldosterone antagonist, and an endothelin-1 blocking agent to the diagnosed individual.

8. The method of claim 7, wherein the individual is at risk for heart failure.

9. The method of claim 7, wherein said step of quantifying comprises calculating the concentration of IGFBP-7 in the control sample having a specificity of at least 95%, the specificity calculated from an unaffected subgroup of samples.

10. The method of claim 7, wherein said step of providing the diagnosis is performed by a computing device.

11. The method of claim 7, wherein said step of quantifying the signal is performed by a computing device.

12. The method of claim 7, wherein the detectable label comprises one of a peroxidase conjugate and digoxigenin.

13. The method of claim 7, wherein prior to the step of diagnosing, the method further comprises:
    contacting a portion of the sample with an antibody having specific binding affinity for NT-proBNP, thereby forming a complex between the antibody and NT-proBNP the antibody having a detectable label;
    separating the complex formed in said step of contacting from antibody not comprising the complex;
    quantifying a signal from the detectable label of the antibody comprising the complex formed in said step of contacting, the signal being proportional to an amount of NT-proBNP in the sample, whereby a concentration of NT-proBNP in the sample is calculated;

comparing the concentration of NT-proBNP calculated in said step of quantifying to a concentration of NT-proBNP in a control sample comprising one or more healthy individuals;

and the step of providing diagnosis is replaced with:

providing a diagnosis of heart failure in the individual when the concentration of both IGFBP-7 calculated in the sample is greater than the concentration of IGFBP-7 in the control sample and the concentration of NT-proBNP calculated in the sample is greater than the concentration of NT-proBNP in the control sample.

14. The method of claim 7, wherein prior to the step of providing a diagnosis, the method further comprises:

contacting a portion of the sample with an antibody having specific binding affinity for troponin T, thereby forming a complex between the antibody and troponin T the antibody having a detectable label;

separating the complex formed in said step of contacting from antibody not comprising the complex;

quantifying a signal from the detectable label of the antibody comprising the complex formed in said step of contacting, the signal being proportional to an amount of troponin T in the sample, whereby a concentration of troponin T in the sample is calculated;

comparing the concentration of troponin T calculated in said step of quantifying to a concentration of troponin T in a control sample comprising one or more healthy individuals; and the step of providing diagnosis is replaced with:

providing a diagnosis of heart failure in the individual when the concentration of both IGFBP-7 calculated in the sample is greater than the concentration of IGFBP-7 in the control sample and the concentration of troponin T calculated in the sample is greater than the concentration of troponin T in the control sample.

15. The method of claim 7 further comprising the step of:

contacting the portion of the sample from the subject with a capture antibody, the capture antibody having specific binding affinity for an epitope of IGFBP-7 not bound by the antibody, thereby forming a complex between the capture antibody and IGFBP-7, the capture antibody coupled to one of streptavidin and biotin, said step of contacting the portion of the sample with the capture antibody occurring prior to said steps of separating and quantifying, wherein upon said steps of contacting the portion of the sample with the antibody and contacting the portion of the sample with the capture antibody, a complex between the antibody, IGFBP-7 and the capture antibody is thereby formed.

16. The method of claim 15, wherein the capture antibody comprises one of avidin or biotin.

17. The method of claim 16, wherein said step of separating comprises contacting the complex between the antibody, IGFBP-7 and the capture antibody with a solid surface coupled to the other of avidin and biotin.

* * * * *

UNITED STATES PATENT AND TRADEMARK OFFICE
CERTIFICATE OF CORRECTION

PATENT NO. : 10,488,422 B2  
APPLICATION NO. : 15/285685  
DATED : November 26, 2019  
INVENTOR(S) : Ursula-Henrike Wienhues-Thelen et al.

Page 1 of 1

It is certified that error appears in the above-identified patent and that said Letters Patent is hereby corrected as shown below:

On the Title Page

Page 2, Column 1, item (56), other publications, Line 2 cite no. 1, delete "Proein" and insert --Protein--, therefor.

Signed and Sealed this  
Twenty-fourth Day of November, 2020

Andrei Iancu  
*Director of the United States Patent and Trademark Office*

SEQUENCE LISTING

```
<160> NUMBER OF SEQ ID NOS: 1

<210> SEQ ID NO 1
<211> LENGTH: 282
<212> TYPE: PRT
<213> ORGANISM: Homo sapiens

<400> SEQUENCE: 1

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
                100                 105                 110

Cys Lys Ser Arg Tyr Pro Val Cys Gly Ser Asp Gly Thr Thr Tyr Pro
            115                 120                 125

Ser Gly Cys Gln Leu Arg Ala Ala Ser Gln Arg Ala Glu Ser Arg Gly
        130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
                180                 185                 190

Trp Asn Lys Val Lys Arg Gly His Tyr Gly Val Gln Arg Thr Glu Leu
            195                 200                 205
```

```
Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
            275                 280
```